US005840691A

United States Patent [19]
Furcht et al.

[11] Patent Number: 5,840,691
[45] Date of Patent: Nov. 24, 1998

[54] METHOD FOR TREATING ISCHEMIA USING POLYPEPTIDES WITH FIBRONECTIN ACTIVITY

[76] Inventors: Leo T. Furcht, 2100 W. 21st St., Minneapolis, Minn. 55405; James B. McCarthy, 2555 37th Ave. S., Minneapolis, Minn. 55406; Sharon M. Wahl, 17121 Longdraft, Gaithersburg, Md. 20878; Janice B. Allen, 215 S. Main St., Wendell, N.C. 27591; Kevin L. Billups, 5505 Dufferin Dr., Savage, Minn. 55378; Jeffrey E. Everett, 1180 Benton Way, Arden Hills, Minn. 55112

[21] Appl. No.: 480,133

[22] Filed: Jun. 7, 1995

Related U.S. Application Data

[63] Continuation-in-part of Ser. No. 139,903, Oct. 21, 1993, abandoned, which is a continuation-in-part of Ser. No. 990,296, Dec. 10, 1992, Pat. No. 5,591,719.

[51] Int. Cl.$^6$ .......................... A61K 38/04; A61K 38/08; A61K 38/10; A61K 38/16
[52] U.S. Cl. ............................... 814/12; 514/13; 514/14; 514/15; 514/16; 530/324; 530/326; 530/328
[58] Field of Search .................................. 514/12, 13, 14, 514/15, 16; 530/324, 326, 328

[56] References Cited

U.S. PATENT DOCUMENTS

| | | | |
|---|---|---|---|
| 4,587,046 | 5/1986 | Goodman et al. | 530/330 |
| 5,037,673 | 8/1991 | Kupecek et al. | 525/54.1 |
| 5,037,683 | 8/1991 | Kupecek et al. | 428/36.7 |

OTHER PUBLICATIONS

Ruoslahti E. J. Clin. Invest., 87, 1–5, Jan. 1991.
Osborn et al. Cell., 6, 3–6, Jan. 1990.
Ruosalahti, et al., Science, 238, 491–497, 1987.
Alspaugh, et al., Textbook of Rheumatology, (W.N. Kelly, E.D. Harris, B. Ruddy, et al. eds.) W.B. Saunders, Philadelphia, PA, Chap. 62, pp. 971–999 (1981).
Arai, et al., Annu. Rev. Biochem., 59, 783–836, (1990).
Argos, EMBO Journal, 8, 779–785, (1989).
Bauminger et al., Methods in Enzymology, 70, 151–159 (1980).
Boivin, et al., American Journal of Pathology, 146, 276–288, (1995).
Border, et al., J. Clin. Invest., 90, 1–7, (1992).
Brennan, et al., Curr. Opin. Immunol., 4, 754–759, (1992).
Christ, et al., J. of Immunol., 153, 1936–1946, (1994).
Chromartie et al., J. Exp. Med., 146, 1585 (1977).
Dang, et al., Arthritis & Rheumatism, 37, S278 (1994).
Dayhoff, et al., Methods in Enzymology, 91, 524–545, (1983).
Fox, et al., J. of Immunol., 152, 5504–5592 (1994).
Fox, et al., Rheumatic Disease Clinics of North America, 18, 517–538 (1992).
Frazier–Jessen, et al., FASEB Journal, 9, A814 (1995).
Geiser et al., Proc. Natl. Acad. Sci. USA, 90, 9944–9948 (1993).
Gribskov, et al., Nucleic Acids Research, 14, 6745–6763 (1986).
Hamano, et al., Eur. J. Immunol., 23, 2387–2391 (1993).
Haneji, et al., J. of Immunol., 153, 2769–2777 (1994).
Hartwell, et al., Immunology Letters, 43, 15–21 (1994).
Hayashi, et al., Pathology International, 44, 559–568 (1994).
Hines, et al., Proc. Natl. Acad. Sci. USA, 91, 5187–5191 (1994).
Jabs, et al., Lacrimal Gland, Tear Film, and Dry Eye Syndromes, (Edited by D.A. Sullivan, Plenum Press, New York), 623–630 (1994).
Klinman, et al., J. of Experimental Medicine, 165, 1755–1760 (1987).
Klinman, J. of Clin. Investigation, Inc., 86, 1249–1254 (1990).
Kobayashi, et al., Cardiovascular Surgery, 1, 577–582 (1993).
Kulkarni, et al., Am. J. Pathol., 146, 264–275 (1995).
Laing, et al., Stroke, 24, 294–298 (1993).
Lampe, et al., J. of Immunol., 147, 2902–2906 (1991).
Leff, Bio. World Today, 5, 1–5 (1994).
Letterio et al., Science, 264, 1936–1938 (1994).
Llorente, et al., Eur. Cytokine Netw., 4, 421–430 (1993).
Longa, et al., Stroke, 20, 84–91 (1989).
Mathison, et al., Immunology Today, 15, 527–532 (1994).
Matsuo, et al., Stroke, 25, 1469–1475 (1994).
McCartney–Francis, et al., J. of Leukocyte Biology, 55, 401–409 (1994).
Montgomery, et al., J. of Immunology, 147, 554–560 (1991).
Nagafuchi, et al., J. of Immunology, 151, 6525–6534 (1993).
Ono, et al., J. Thoracic and Cardiovascular Surgery, 57, 225–229 (1969).
Shirai, et al., J. of Immunology, 153, 1879–1894 (1994).
J.B. Allen, et al., J. Clin. Invest, 76, pp. 1042–1056 (1985).
M.E. Brandes, et al., J. Clin. Invest., 87, pp. 1108–1113 (1991).
A.B. Kulkarni, et al., Proc. Natl. Acad. Sci., 90, pp. 770–774 (1993).
E. F. Remmers, et al., Growth Factors, 2, pp. 179–188 (1990).
U. S. Ryan, et al., J. tissue Cult. Method, 10, pp. 3–5 (1986).
H. Sano, et al., J. Clin. Invest., 91, pp. 553–565 (1993).
S. M. Wahl, et al., Proc. Natl. Acad. Sci., 90, pp. 4577–4581 (1993).

(List continued on next page.)

Primary Examiner—Cecilia J. Tsang
Assistant Examiner—Michael L. Borin
Attorney, Agent, or Firm—Merchant, Gould, Smith, Edell, Welter & Schmidt

[57] ABSTRACT

Methods for treating ischemia using polypeptides with fibronectin related activity are provided. The methods involve administering an effective amount of one or more polypeptides which include an amino acid sequence corresponding substantially to isolated amino acid sequence from the 33 kD carboxy terminal heparin-binding region located on the A chain of fibronectin or an RGD-containing amino acid sequence within the 11.5 kD RGDS-mediated cell adhesion region located on all isoforms of fibronectin.

16 Claims, 17 Drawing Sheets

OTHER PUBLICATIONS

S. M. Wahl, *J. Clin. Immunol.,* 12, pp. 61–74 (1992).
S. M. Wahl, et al., *Immunol. Today,* 10, pp. 258–261 (1989).
A. Woods, et al., *Mol. Biol. of the Cell,* 4, pp. 605–613 (1993).
S. M. Albelda et al., FASEB J., 4, 2868–2880 (1990).
J. B. Allen et al., *Cytokine,* 3, 98–106 (1991).
J. B. Allen et al., *J. Clin. Invest.,* 76: 1042–1056 (1985).
M. Aumailley et al., *J. Cell. Biol.,* 103, 1569–1576 (1986).
W. Babel et al., *Eur. J. Biochem.,* 143, 545–556 (1984).
M. E. Brandes et al., *J. Clin. Invest.,* 87, 1108–1113 (1991).
D. Brazel et al., *Eur. J. Biochem.,* 168, 529–536 (1987).
D. Brazel et al., *Eur. J. Biochem.,* 172, 35–42 (1988).
J. M. Brinker et al., *Proc. Natl. Acad. Sci. USA,* 82, 3649–3653 (1985).
J. P. Case, et al., *Am. J. Pathology,* 135 (6), pp. 1055–1064 (1989).
J. P. Case, et al., *J. Clin. Invest.,* 84, pp. 1731–1740 (1989).
M. K. Chelberg et al., *Cancer Research,* 49, 4796–4802 (1989).
Z. Dische et al., *J. Bio. Chem.,* 175, 595–603 (1948).
L. Furcht et al., *Biochem. and Molec. Genetics of Cancer Metastasis,* K. Lapis et al., eds. (1985) at pp. 43–53.
L. T. Furcht, *Modern Cell Biology,* vol. 1, B. Satir, ed., Alan R. Liss, Inc., New York (1983) at pp. 53–117.
A. Garcia–Pardo et al., *Biochem. J.,* 241, 923–928 (1987).
A. Garcia–Pardo et al., *Immunology,* 69, 121–126 (1990).
R. W. Glanville et al., *Eur. J. Biochem.,* 152, 213–219 (1985).
T. J. Herbst et al., *J. Cell Biol.,* 106, 1365–1373 (1988).
R. M. Hewick et al., *J. Biol. Chem.,* 256, 7990–7997 (1981).
M. J. Humphries et al., *J. Biol. Chem.,* 262, 6886–6892 (1987).
H. E. Kambic et al., *Chem. and Eng. News,* pp. 30–48 (Apr. 14, 1986).
G. G. Koliakos et al., *J. Biol. Chem.,* 264, 2313–2323 (1989).
A. R. Kornblihtt et al., *EMBO J.,* 4, 1755–1759 (1985).
M. Kurkinen et al., *J. Biol. Chem.,* 259, 5915–5922 (1984).
J. Kyte et al., *J. Mol. Biol.,* 157, 105–132 (1982).
A. Laffon et al., *J. Clin. Invest.,* 88, 546–552 (1991).
S. M. Louis et al., *Neuroscience,* 39, 727–731 (1990).
J. B. McCarthy et al., *Biochemistry,* 27, 1380–1388 (1988).
J. B. McCarthy et al., *J. Cell. Biol.,* 102, 179–188 (1986).
J. B. McCarthy et al., *J. Natl. Cancer Inst.,* 80, 108–116 (1988).
J. C. Murray et al., *J. Cell. Biol.,* 80, 197–202 (1979).
G. Muthukumaran et al., *J. Biol. Chem.,* 264, 6310–6317 (1989).
I. Oberb umer et al., *Eur. J. Biochem.,* 147, 217–224 (1985).
H. Pande et al., *Eur. J. Biochem.,* 162, 403–411 (1987).
T. E. Petersen et al., *Proc. Nat'l. Acad. Sci. USA,* 80, 137–141 (1983).
M. D. Pierschbacher et al., *Proc. Nat'l. Acad. Sci. USA,* 81, 5985–5988 (1984).
M. D. Pierschbacher et al., *Nature,* 309, 30–33 (1984).
T. Pihlajaniemi et al., *J. Biol. Chem.,* 260, 7681–7687 (1985).
E. F. Remmers, et al., *Seminars in Arthr. and Rheum.,* 21 (3), pp. 191–199 (1991).
S. L. Rogers et al., *Devel. Biol.,* 98, 212–220 (1983).
E. Ruoslahti, *J. Clin. Invest.,* 87, 1–5 (1991).
H. Sano, et al., *J. Clin. Invest.,* 89, pp. 97–108 (1992).
J. Saus et al., *J. Biol. Chem.,* 264, 6318–6324 (1989).
S. M. Schwartz, *In Vitro,* 14, 966–980 (1978).
U. Schwarz–Magdolen et al., *FEBS Lett.,* 208, 203–207 (1986).
J. E. Schwarzbauer et al., *Cell,* 35, 421–431 (1983).
D. M. Shotten et al., *J. Mol. Biol.,* 131, 303–329 (1979).
D. E. Smith et al., *J. Biol. Chem.,* 257, 6518–6523 (1982).
R. Soininen et al., *FEBS Lett.,* 225, 188–194 (1987).
T. A. Springer, *Nature,* 346, 425–434 (1990).
S. P. Sugrue, *J. Biol. Chem.,* 262, 3338–3343 (1987).
R. Timpl et al., *New Trends in Basement Membrane Research,* K. Kuehn et al., eds., Raven Press, NY (1982) at pp. 57–67.
K. J. Tomaselli et al., *J. Cell. Biol.,* 105, 2347–2358 (1987).
E. C. Tsilibary et al., *J. Cell. Biol.,* 103, 2467–2473 (1986).
E. C. Tsilibary et al., *J. Biol. Chem.,* 263, 19112–19118 (1988).
R. L. Wilder, et al., *J. Cell. Biochem.,* 45, pp. 162–166 (1991).
R. L. Wilder, et al., *Clin. Orthopaedics and Related Research,* 265, pp. 36–41 (1991).
X–d. Yang et al., *J. Autoimmun.,* 3, 11–23 (Feb. 1990).
Loft, B. World Today, Oct. 28, 1994, vol. 5, No. 210 pp. 1 + 5.

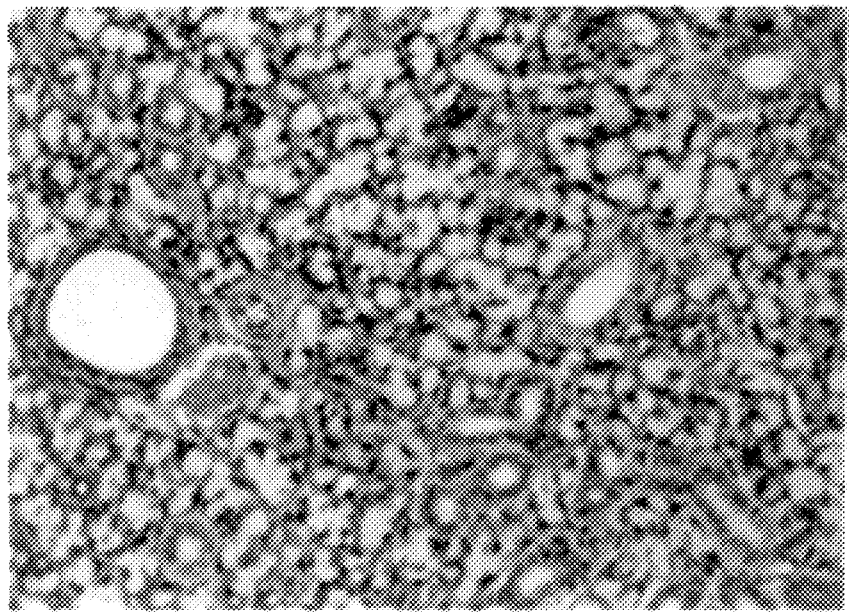
FIG. 15A  TGF-β1(+/+)
FIG. 15B  TGF-β1(-/-)

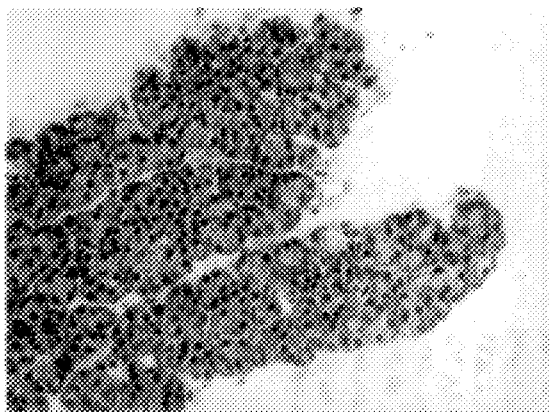
FIG. 19A  TGF-β1(+/+)
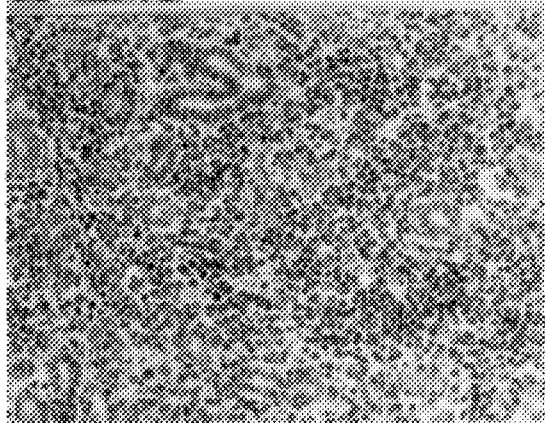
FIG. 19B  TGF-β1(-/-)
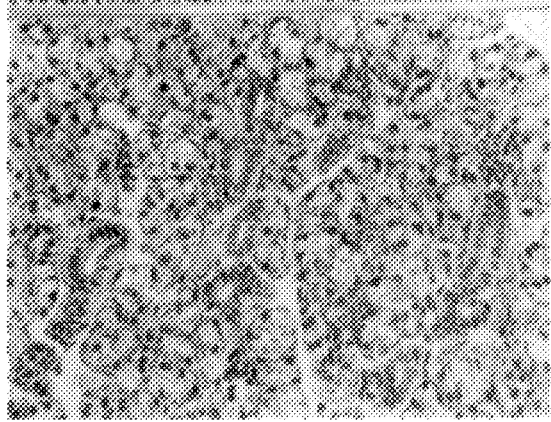
FIG. 19C  TGF-β1(-/-) + FN peptides

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

```
Tyr  Glu  Lys  Pro  Gly  Ser  Pro  Pro  Arg  Glu  Val  Val  Pro  Arg  Pro  Arg
1                  5                            10                           15
Pro  Gly  Val
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

Lys Asn Asn Gln Lys Ser Glu Pro Leu Ile Gly Arg Lys Lys Thr
 1               5                   1 0                  1 5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Trp Gln Pro Pro Arg Ala Arg Ile
 1               5

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

Asp Glu Leu Pro Gln Leu Val Thr Leu Pro His Pro Asn Leu His Gly
 1               5                   1 0                  1 5

Pro Glu Ile Leu Asp Val Pro Ser Thr
                2 0                 2 5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Ser Pro Pro Arg Arg Ala Arg Val Thr
 1               5

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

Ile Thr Val Tyr Ala Val Thr Gly Arg Gly Asp Ser Pro Ala Ser Ser
 1               5                   1 0                  1 5

Lys Pro Ile Ser
                2 0

( 2 ) INFORMATION FOR SEQ ID NO:7:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

CTGCTCTTAC TGACTGGCAT GA 22

( 2 ) INFORMATION FOR SEQ ID NO:8:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

TCAAATGCTC CTTGATTTCT GGGC 24

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

AGCTTTCAGC TCATATGGGT CCGACAGCAC 30

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

CTTCTGCATG TCTGTTGTGG TTTGTTGCTC 30

( 2 ) INFORMATION FOR SEQ ID NO:11:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GTCGCATCCG TGGATATGGC TCCTGGTACA 30

( 2 ) INFORMATION FOR SEQ ID NO:12:

( i ) SEQUENCE CHARACTERISTICS:
( A ) LENGTH: 18 base pairs
( B ) TYPE: nucleic acid
( C ) STRANDEDNESS: single

```
          ( D ) TOPOLOGY: linear ( i i ) MOLECULE TYPE: DNA (genomic)

( x i ) SEQUENCE DESCRIPTION: SEQ ID NO:12:

CATTTCCACG ATTTCCCA                                                              1 8

( 2 ) INFORMATION FOR SEQ ID NO:13:

( i ) SEQUENCE CHARACTERISTICS:
              ( A ) LENGTH: 22 base pairs
              ( B ) TYPE: nucleic acid
              ( C ) STRANDEDNESS: single
              ( D ) TOPOLOGY: linear ( i i ) MOLECULE TYPE: DNA (genomic)

( x i ) SEQUENCE DESCRIPTION: SEQ ID NO:13:

GGAGTCGGTT AGCAGTATGT TG                                                         2 2

( 2 ) INFORMATION FOR SEQ ID NO:14:

( i ) SEQUENCE CHARACTERISTICS:
              ( A ) LENGTH: 4 amino acids
              ( B ) TYPE: amino acid
              ( C ) STRANDEDNESS:
              ( D ) TOPOLOGY: linear ( x i ) SEQUENCE DESCRIPTION: SEQ ID NO:14:

Arg Gly Asp Ser
1

( 2 ) INFORMATION FOR SEQ ID NO:15:

( i ) SEQUENCE CHARACTERISTICS:
              ( A ) LENGTH: 4 amino acids
              ( B ) TYPE: amino acid
              ( C ) STRANDEDNESS:
              ( D ) TOPOLOGY: linear ( x i ) SEQUENCE DESCRIPTION: SEQ ID NO:15:

Arg Ala Arg Ile
1
```

METHOD FOR TREATING ISCHEMIA USING POLYPEPTIDES WITH FIBRONECTIN ACTIVITY

CROSS REFERENCE TO RELATED APPLICATION

This application is a Continuation-in-Part of application Ser. No. 08/139,903, filed Oct. 21, 1993, now abandoned which is a Continuation-in-Part of application Ser. No. 07/990,296, filed Dec. 10, 1992.

GOVERNMENT SUPPORT

The present invention was made with the support of Grant Nos. CA43924 and CA21463 from the National Institutes of Health. The government has certain rights in the invention including those under the grants noted above.

BACKGROUND OF THE INVENTION

The adhesion of mammalian cells to the extracellular matrix and other cells is of fundamental importance in regulating growth, adhesion, motility and the development of proper cellular phenotype. This has implications for normal development, wound healing, immunity, chronic inflammatory diseases, and tumor metastasis. Evidence accumulated over the last several years suggests that the molecular basis for the adhesion of both normal and transformed cells is complex and probably involves several distinct cell surface molecules. Extracellular matrices consist of three types of macromolecules: collagens, proteoglycans and noncollagenous glycoproteins. The extracellular matrix molecule which has been most intensively studied with regard to cell adhesion is the noncollagenous cell adhesion glycoprotein, fibronectin, which is present in plasma, cell matrices, basal lamina and on cell surfaces. The fibronectin from plasma consists of a disulfide-bonded dimer having a molecular weight of 450,000 daltons. The two subunit chains ("A" and "B"), each of about 220,000 daltons, are observed under reducing conditions. This form of fibronectin will be referred to as "fibronectin" hereinafter.

Polypeptides from a 33 kD carboxyl terminal heparin-binding fragment of the A subunit fibronectin which promote adhesion and spreading of endothelial cells and melanoma cells are described in U.S. Pat. Nos. 4,839,464 and 5,019,646. The synthetic polypeptides corresponding to fibronectin residues described in these patents are disclosed as useful to (a) assist in nerve regeneration, (b) promote wound healing and implant acceptance, (c) promote cellular attachment to culture substrata, and (d) inhibit metastasis of malignant cells.

Evolution of inflammatory and immune reactions is dependent upon the recruitment and migration of circulating leukocytes to sites of injury or antigen deposition. The accumulation of leukocytes is dependent not only on chemotactic signals emanating from the inflammatory site, but also on cell-cell and cell-matrix interactions. Many of these cellular and matrix interactions are dependent upon expression of cell surface adhesion molecules (CAMs) such as integrins, cell surface proteoglycans, selecting, which facilitate targeting and retention of circulating cells to sites of immunologic challenge (see e.g., T. Springer, Nature, 346: 425–434 (1990); S. M. Albeda et al., FASEB J., 4: 2668–2680 (1990); Ruoslahti, J. Clin. Invest., 87: 1–5 (1991)).

Integrins represent a family of cell surface $\alpha\beta$ heterodimeric proteins that mediate cell adhesion to other cells and to extracellular matrix constituents, including fibronectin. Although the role of integrins and other CAMs in mediating arrest and adhesion of inflammatory cells prior to extravasation is complex and poorly understood, emerging evidence suggests that integrins may be pivotal in these events. Therefore, a need exists for a method employing an agent that inhibits or modulates emigration of circulating cells to the site of immunologic challenge as a mechanism to regulate inflammation and its associated disorders.

SUMMARY OF THE INVENTION

The present invention provides a method for treating a number of disease states such as, for example, conditions associated with inflammatory diseases, by administering to the patient an effective amount of a composition containing a polypeptide having a sequence of at least about three amino acids corresponding substantially to an amino acid sequence within the 33 kD carboxyl terminal heparin-binding region located on the A chain of fibronectin or an RGD-containing amino acid sequence within the 11.5 kD RGDS-mediated cell adhesion region located on all isoforms of fibronectin. Preferably, the method involves administering an effective amount of a polypeptide or mixture of polypeptides having the formula:

tyr-glu-lys-pro-gly-ser-pro-pro-arg-glu-val-val-pro-arg-pro-arg-pro-gly-val (I) [SEQ ID NO: 1], lys-asn-asn-gln-lys-ser-glu-pro-leu-ile-gly-arg-lys-lys-thr (II) [SEQ ID NO: 2], trp-gln-pro-pro-arg-ala-arg-ile (V) [SEQ ID NO: 3], asp-glu-leu-pro-gln-leu-val-thr-leu-pro-his-pro-asn-leu-his-gly-pro-glu-ile-leu-asp-val-pro-ser-thr (CS-1) [SEQ ID NO: 4], and ser-pro-pro-arg-arg-ala-arg-val-thr (IV) [SEQ ID NO: 5].

Polypeptide I formula represents isolated fibronectin residues 1906–1924. Polypeptide II represents isolated fibronectin residues 1946–1960. Polypeptide IV represents isolated fibronectin residues 1784–1792. Polypeptide V represents isolated fibronectin residues 1892–1899. Polypeptide CS-1 corresponds to fibronectin residues 1961–1985.

Another useful polypeptide in the method of the present invention is:

ile-thr-val-tyr-ala-val-thr-gly-arg-gly-asp-ser-pro-ala-ser-ser-lys-pro-ile-ser (MC-2) [SEQ ID NO: 6]. This polypeptide corresponds to fibronectin residues 1485–1504. With the exception of CS-1, all other peptides are common to all isoforms of fibronectin.

According to the present invention, a polypeptide or mixture of polypeptides corresponding to an isolated region of fibronectin residues is employed to suppress inflammation and tissue destruction.

One embodiment of the present invention provides a method of treating arthritis or an immune-mediated disorder which includes administering a polypeptide or mixture of polypeptides corresponding substantially to an isolated region of fibronectin. The present invention also includes embodiments directed to treatments for rheumatoid arthritis, acute respiratory distress syndrome ("ARDS"), Sjögren's syndrome, lupus erythematosus, graft-vs.-host disease, graft rejection, and ischemia. These treatments also include the administration of a polypeptide corresponding substantially to a fibronectin fragment.

In one preferred embodiment, the present method provides a method for treating graft rejection which typically includes administering an effective amount of a polypeptide selected from the group of compounds having the formula: trp-gln-pro-pro-arg-ala-arg-ile [SEQ ID NO: 3], asp-glu-leupro-gln-leu-val-thr-leu-pro-his-pro-asn-leu-his-gly-pro-glu-ile-leu-asp-val-pro-ser-thr [SEQ ID NO: 4] and ile-thr-val-tyr-ala-val-thr-gly-arg-gly-asp-ser-pro-ala-ser-ser-lys-pro-ile-ser [SEQ ID NO: 6]. The treatment may involve the administration of one of the three fibronectin related polypeptides or the three polypeptides may be administered as a mixture.

Another embodiment of the present invention employs multivalent polypeptide and carrier compound conjugates. For example, conjugates having at least 3 and typically 4 to 8 polypeptide fragments covalently bound to a carrier compound, such as albumin (e.g., ovalbumin (OA), human serum albumin (HSA)), other proteins, polyethylene glycol (PEG), a lipid or a cellulose derivative, are useful in the present invention.

The present method may be employed to treat acute inflammatory disorders and is particularly well-suited to treat chronic inflammatory disorders and immune mediated disorders. In addition to providing treatments for graft rejection, ARDS and ischemia, the present method is especially useful for treating autoimmune disorders. Examples of autoimmune disorders which may be treated using the present method include Sjögren's syndrome, graft-vs.-host disease and connective tissue disorders such as rheumatoid arthritis, lupus erythematosus. Since it is expected that further digestion/hydrolysis of polypeptides from the 33 kD carboxyl portion of the A chain of fibronectin or the RGD-containing amino acid sequence within the 11.5 kD RGDS-mediated cell adhesion region of fibronectin will yield fragments of substantially equivalent bioactivity, lower molecular weight polypeptides corresponding to isolated residues of the A chain of fibronectin are considered to be within the scope of the present invention. While the method described herein utilizes fibronectin polypeptides I, II, IV, V, CS-1 and MC-2, it is to be understood that polypeptides having shorter sequences of amino acids, as well as other polypeptides corresponding substantially to regions within the A and/or B chains of fibronectin with functionally active sequences, are within the scope of the invention. For example, polypeptides having sequences of about 3 amino acids or larger with functionally active sequences are within the scope of the invention. Examples of such short fragment polypeptides include arg-gly-asp (RGD), arg-gly-asp-ser (RGDS) and other RGD-containing tetramers. It is known that trimers such as RGD when connected to other amino acids or amino acid sequences are functionally active (e.g., the Ser of RGDS may be substituted to form a functionally active tetramer). Other examples of functionally active small polypeptides within the scope of the invention include ala-arg-ile (ARI), arg-ala-arg-ile (RARI) and other short ARI-containing sequences.

BRIEF DESCRIPTION OF THE DRAWINGS

FIG. 15A and 15B shows the submandibular salivary gland in a TGF-β1 (+/+) mouse (A) and a TGF-β1 (−/−)

mouse (B). The submandibular glands of the symptomatic TGF-β1 (−/−) mouse (C) shows large numbers of mononuclear cells, primarily lymphocytes and plasma cells, accumulated in a periductal fashion. Some aggregates are sharply demarcated from adjacent tissue and resemble lymphoid follicles. Whereas the lobular structure of the gland is preserved in most cases, the internal organization of acini and ducts is disrupted with atrophy and disappearance of acini and does not resemble a normal submandibular gland (B).

Figure 16:
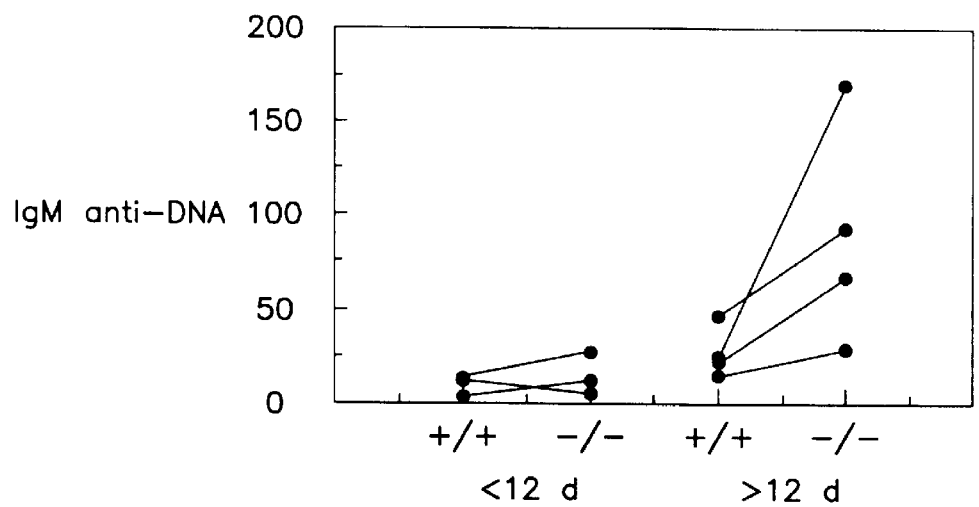

FIG. 16 shows the levels of anti-DNA antibodies detected in plasma from TGF-β1 null mice (−/−) versus the levels observed in normal littermates (+/+).

Figure 17:
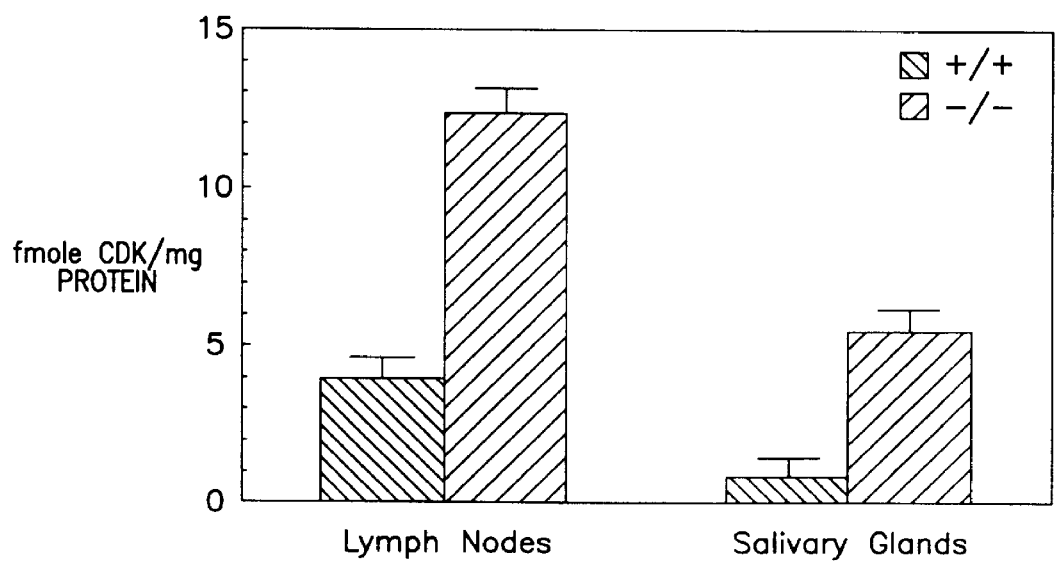

FIG. 17 shows the results of ELISA assays for CDK, a cell cycle control enzyme, in homogenates CDK from the salivary gland and lymph node of TGF-β1 null mice (−/−) and normal littermates (+/+).

Figure 18:
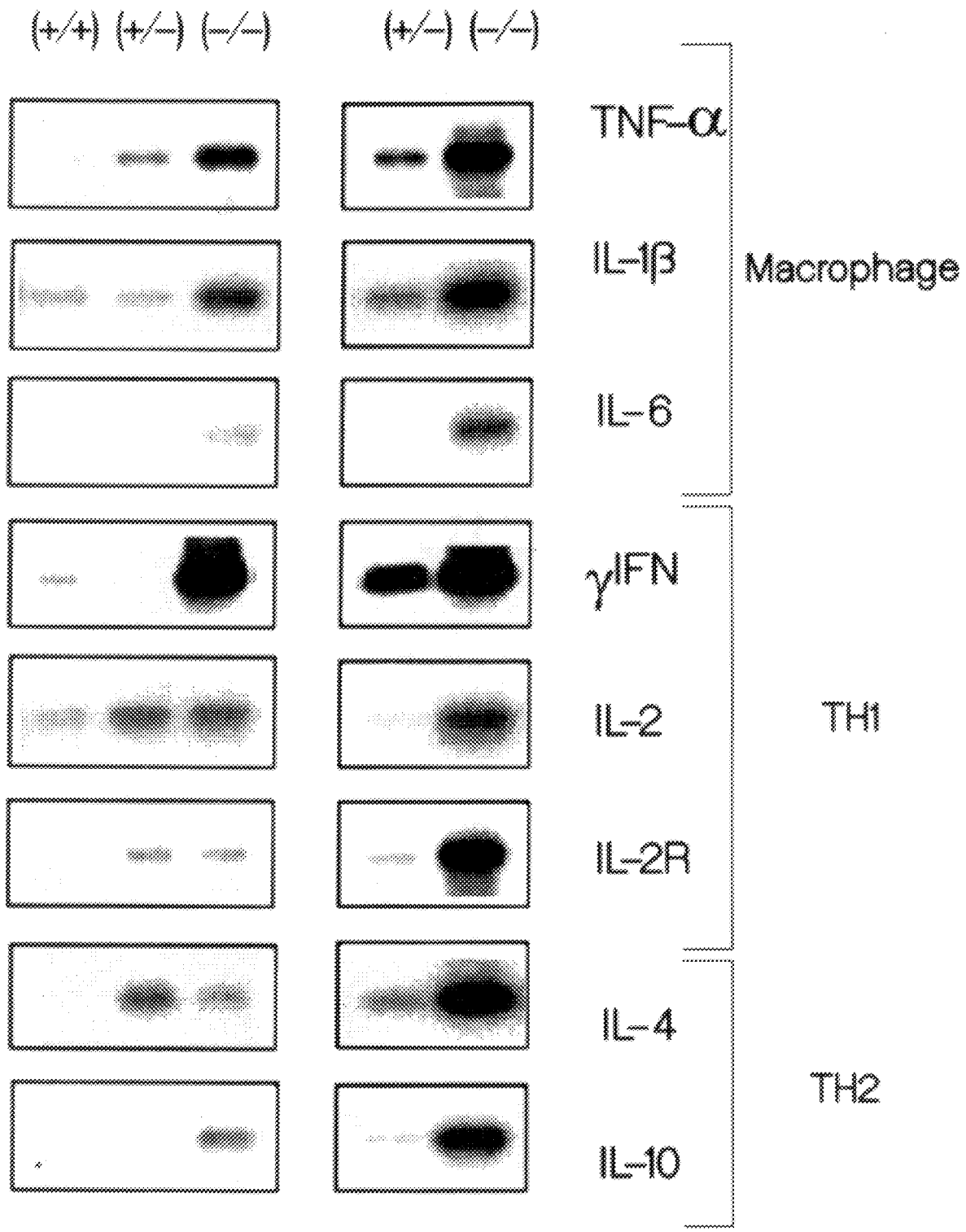

FIG. 18 shows Southern blots of cytokine mRNA expression in submandibular glands of symptomatic TGF-β1 (−/−) mice and their heterozygous [TGF-β1 (±)] and normal (+/+) littermates as evaluated by reverse transcriptase-PCR. The data represent two litters of mice (21 days old).

FIG. 19(A–C) show the salivary glands obtained from a wild-type TGF-β1 (+/+) mouse (A), a symptomatic TGF-β1 (−/−) mouse (B), and a TGF-β1 (−/−) mouse that received daily injections of four FN peptides (C). The tissue from the untreated TGF-β1 null mouse shows extensive inflammation, tissue disruption and acinar atrophy. Salivary gland tissue from the TGF-β1 (−/−) mouse that received daily injections of the FN peptides shows no inflammation and normal structural architecture (compare (C) with (A)).

DETAILED DESCRIPTION OF THE INVENTION

Structure of Fibronectin

The structure of fibronectin has been previously described in U.S. Pat. Nos. 4,839,464 and 5,019,646, the disclosures of which are incorporated by reference herein. The A chain digest contains a 11.5 kD RGDS-mediated cell adhesion fragment (domain IV), a 33 kD fragment (domain V) and a 31 kD fragment (domain VI). The polypeptides useful for the present invention correspond substantially to isolated regions of domains IV and V, which are common to all isoforms of fibronectin.

Domain IV is a 11.5 kD polypeptide of 108 amino acid residues corresponding to residues 1410–1517 of all isoforms of fibronectin. Domain V of fibronectin has been previously described in McCarthy et al., *J. Cell Bio.*, 102, 179–188 (1986) and U.S. Pat. Nos. 4,839,464 and 5,019,646, the disclosure of which are incorporated by reference herein. Domain V is a 33 kD polypeptide of 157 amino acid residues corresponding to residues 1583–2039 of plasma fibronectin.

The present fibronectin related polypeptides are typically relatively small polypeptides, e.g., include no more than about 100 amino acid residues, as such small polypeptides can be readily synthesized by common techniques. The fibronectin related polypeptides preferably include no more than about 50 amino acids and, most preferably, include no more than about 25 amino acids. The present polypeptides typically represent fragments including sequences of at least about 8 amino acids corresponding substantially to a sequence within the 33 kD carboxyl terminal, heparin-binding region located on the A chain of fibronectin or to an RGD-containing fragment within the 11.5 kD RGDS-mediated cell adhesion region of fibronectin. Functionally active polypeptides having shorter amino acid sequences are, however, within the scope of the present invention. For example, polypeptides having sequences of less than 8 amino acids, e.g., polypeptides including an amino acid sequence corresponding substantially to a sequence of at least about 3 and, preferably, at least about 5 amino acids from within one of the fibronectin region noted above, are within the scope of the present invention where such polypeptides modulate cellular adhesion and/or mediate cell migration. In particular, the polypeptides employed in the present method are capable of suppressing adhesion of leukocytes to endothelial cells and/or extracellular matrix.

As used herein, the definition of polypeptides "corresponding substantially to" a specific amino acid sequence within fibronectin includes peptides which correspond to variants or mutants of the specific amino acid sequence. The variants and mutants typically possess a high degree of sequence homology with the specified sequence (e.g., substitution, deletion or insertion mutants). In addition to corresponding substantially to a specific amino acid sequence within fibronectin, the present polypeptides are capable of modulating the adhesion and/or migration of inflammatory cells (e.g., leukocytes). Preferably, the polypeptides are capable of inhibiting the adhesion of inflammatory cells to endothelial cells and/or cell surface adhesion molecules.

For the purposes of this application, polypeptides "corresponding substantially to" a specific amino acid sequence within fibronectin include sequences which modulate cellular adhesion and have at least 70% homology and, typically, at least 90% homology with the selected fibronectin fragment. Preferably, polypeptides "corresponding substantially to" a specific amino acid sequence within fibronectin include sequences which have at least 50% identity and, more preferably, at least 80% identity with the selected fibronectin fragment. Fibronectin related fragments in which the primary amino acid sequence has been augmented by derivatization using sugar molecules or other supplementary molecules, such as lipids or phosphate fragments, are also included in this definition. Alternatively, the primary amino acid sequence may be altered by modification of individual amino acid residues, e.g., sulfhydryl groups modified by carboxymethylation with iodoacetic acid or carboxyl groups modified by carbodiimide activation followed by subsequent derivatization to a corresponding amide. Polypeptides "corresponding substantially to" a specific amino acid sequence within fibronectin also include obvious or trivial variants of the specified sequence which have one or more additional amino acid residues at their amino and/or carboxy terminii. The present invention also includes variants of fibronectin fragments which lack one or more amino acid residues at their amino and/or carboxy terminii. The modifications discussed above may affect the activity of the polypeptide, either by enhancing or diminishing the activity of the polypeptide. The modified polypeptides which correspond substantially to a fibronectin fragment, however, are capable of modulating cellular adhesion and, in particular, are capable of modulating the adhesion of inflammatory cells.

Preferably, polypeptides corresponding substantially to a specific amino acid sequence within fibronectin are modified through deletions or conservative amino acid substitutions. Typically, such conservative amino acid substitutions include substitutions such as described by Dayhoff in the "Atlas of Protein Sequence and Structure," 5, (1978) and by Argos in *EMBO J.*, 8, 779 (1989). For example, the exchange of amino acids within one of the following classes represent conservative substitutions:

Class I: Ala, Gly, Ser, Thr, Pro, (representing small aliphatic side chains and hydroxyl group side chains); Class II: Cys, Ser, Thr and Tyr (side chains including an—OH or —SH group); Class III: Glu, Asp, Asn and Gln (representing carboxyl group containing side chains): Class IV: His, Arg and Lys (representing basic side chains); Class V: Ile, Val, Leu, Phe and Met (representing hydrophobic side chains); Class VI: Phe, Trp, Tyr and His (representing aromatic side chains); and Class VII: Lys, Asp, Glu, Asn and Gln. The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; naphthylalanines, substituted phenylalanines, tetrahydroisoquinoline-3-carboxylic acid, and halogenated tyrosines in Class VI. Larger compilations of related amino acids and amino acid derivatives may be found in a variety of publications known to those skilled in the art, e.g., the catalogue of Bachem Biosciences, Inc. (King of Prussia, Pa.). Moreover, the classes may include both L and D stereoisomers, although L-amino acids are typically preferred for substitutions. As used herein, the term "conservative amino acid substitutions" also includes a number of other amino acid substitutions identified by Gribskov et al., *Nucl. Acid Res.*, 14(16), 6745 (1986) as frequently occurring conservative amino acid substitutions. Included among such conservative amino acid substitutions are the exchange of Ala with Cys, Asp or Glu; the exchange of Gly or His with Asp, Glu or Gln; the exchange of Ser with Asn, Phe or Trp; the exchange of Leu with Tyr or Trp; and the exchange of Pro with Glu, Gln or Arg.

Synthesis of Polypeptides

Polypeptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in *Synthetic Peptides: A User's Guide*, W. M. Freeman & Company, New York, N.Y., pp. 77–183 (1992). The present polypeptides were synthesized from sequences within the 33 kD carboxyl terminal, heparin-binding region located on the A chain of fibronectin or an RGD-containing amino acid sequence within the 11.5 kD RGDS-mediated cell adhesion region located on all isoforms of fibronectin. These polypeptides promote interact with inflammatory cells, such as leukocytes, and preferably, are capable of inhibiting the adhesion of inflammatory cells to endothelial cells and/or cell surface adhesion molecules. The preparation of polypeptides employed in the method of the present invention is described in the above-referenced U.S. Pat. Nos. 4,839,464 and 5,019,646.

The significant chemical properties of peptides useful in the present invention are summarized in Table I, below:

TABLE I

| Peptide | Residue Nos. | Hydropathy Index | Net Charge |
| --- | --- | --- | --- |
| I [SEQ ID NO: 1] | 1906–1924 | −24.3 | +2 |
| II [SEQ ID NO: 2] | 1946–1963 | −32.5 | +2 |
| CS-1 [SEQ ID NO: 4] | 1961–1985 | −9.9 | −4 |
| IV [SEQ ID NO: 5] | 1784–1792 | −12.2 | +3 |
| V [SEQ ID NO: 3] | 1892–1899 | −10.8 | +2 |
| MC-2 [SEQ ID NO: 6] | 1485–1504 | −0.8 | −1 |

The polypeptides used in the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2d ed., 1984), the disclosure of which is incorporated by reference herein. This method of synthesis is understood to be illustrative only and not intended to limit the scope of the present invention in any way.

The Merrifield system of peptide synthesis uses a 1% cross-linked polystyrene resin functionalized with benzyl chloride groups. The halogens, when reacted with the salt of a protected amino acid, will form an ester, linking it covalently to the resin. The benzyloxycarbonyl (BOC) group is used to protect the free amino group of the amino acid. This protecting group is removed with 25% trifluoroacetic acid (TCA) in dichloromethane (DCM). The newly exposed amino group is converted to the free base by 10% triethylamine (TEA) in DCM. The next BOC-protected amino acid is then coupled to the free amine of the previous amino acid by the use of dicyclohexylcarbodiimide (DCC). Side chain functional groups of the amino acids are protected during synthesis by TFA stable benzyl derivatives. All of these peptides of the present invention were synthesized at a University of Minnesota bioengineering facility.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0 M acetic acid, followed by lyophilization of the extract.

Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptides is by amino acid analysis. The polypeptides are first hydrolyzed anaerobically for 24 hours at 110° C. in 6 M HCl (constant boiling) or in 4 N methane sulfonic acid, when cysteine or tryptophan are present. The hydrolyzed amino acids are separated by ion exchange chromatography in an amino acid analyzer using citrate buffers. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981). Peptides may also be modified by amidation or various other means.

Polypeptide Carrier Conjugates

Polypeptides synthesized can be employed in the present invention in a monovalent state, i.e., free polypeptide or a single polypeptide fragment coupled to a carrier molecule. The carrier molecule may include a biological carrier, such as collagen, a glycosaminoglycan, a proteoglycan, albumin, lipids or the like. The carrier molecule may include a synthetic carrier molecule, such as polyethylene glycol (PEG), carbopol or a cellulose derivative (e.g. methylcellulose). Preferably, as described below, to treat chronic inflammatory disorders, conjugates of multiple polypeptide fragments bound to a carrier molecule such as ovalbumin (OA), human serum albumin (HSA), other proteins, PEG, or the like are employed. Such modifications can increase the apparent affinity or change the circulatory half-life of a peptide. The number of polypeptide fragments associated with or bound to each carrier molecule can be varied, but from about 4 to about 8 polypeptide fragments per carrier molecule are typically obtained under standard coupling conditions. Preferably, the polypeptides are employed as a conjugate which includes at least three polypeptides bound to a carrier molecule.

Treatment of Inflammatory Diseases

As noted above, the polypeptides and their compositions modulate inflammation and are therefore useful in the treatment of a number of disease states in which aberrant inflammation plays a detrimental role. The method of the present invention is used to treat patients, most particularly humans afflicted with acute or chronic inflammatory disorders involving ischemia, infection, tissue swelling, and/or bone and cartilage degradation. Inflammatory disease refers to a condition in which activation of leukocytes leads to an impairment of normal physiologic function. Examples of such conditions include acute and chronic inflammation such as osteoarthritis, sepsis, ARDS, immune and autoimmune disorders, rheumatoid arthritis, IBD (inflammatory bowel disease), lupus, MS, graft rejection, cirrhosis, sarcoidosis, granulomatous lesions, periodontitis/gingivitis, graft-vs.-host disease, contact dermatitis, and the like. Included among autoimmune disorders which may be treated using the present method are chronic active hepatitis, Graves' disease, insulin-dependent diabetes mellitus (type I), and Hasshimoto's thyroiditis. Included among inflammatory disorders which may be treated using the present method are inflammatory brain disease, inflammatory demyelinating disease, inflammatory vasculitis, inflammatory myopathies, osteomyelitis, Crohn's disease and interstitial cystitis. Additional examples of inflammatory diseases include myocardial diseases, infectious diseases, pulmonary diseases and graft rejection. Polypeptides corresponding substantially to isolated fibronectin residues can be used to treat inflammatory diseases. Although not necessary to practicing the invention, it is believed that immunosuppressive activity of fibronectin A chain-derived polypeptides blocks leukocyte adhesion to endothelial cells and/or stromal/ parenchymal and/or extracellular matrix, thus affecting leukocyte adhesion, cytokine production and recruitment at sites of inflammation. The method is particularly well suited for treating acute and/or chronic inflammatory disorders, immune mediated disorders, or other disease conditions of the type described above.

Patient treatment using the method of the present invention involves administering therapeutic amounts of the polypeptide composition. In the context of the present invention, the terms "treat" and "therapy" and the like refer to alleviate, slow the progression, prophylaxis, attenuation or cure of existing disease. A polypeptide composition may be formulated with conventional pharmaceutically acceptable parenteral vehicles for administration by injection. These vehicles comprise substances which are essentially nontoxic and nontherapeutic such as water, saline, Ringer's solution, dextrose solution, Hank's solution, or the like. It is to be understood that polypeptide formulations may also include small amounts of adjuvants such as buffers and preservatives to maintain isotonicity, physiological and pH stability. Preferably, the polypeptide or polypeptide carrier molecule conjugate is formulated in purified form substantially free of aggregates and other protein at concentrations ranging from about 0.1 to about 10 mg/ml.

As indicated by the above formulation, the polypeptide may be administered parenterally. In the case of some diseases, the polypeptide can be delivered or administered topically, by transdermal patches, intravenously, intraperitoneally, in aerosol form, orally, or in drops, among other methods. When the polypeptide is administered intravenously, it can be delivered as a bolus or on a continuous basis.

The dose of the polypeptide formulation to be administered will depend upon the patient and the patient's medical history, and the severity of the disease process. However, the dose should be sufficient to alleviate inflammation and/or associated tissue damage of the patient. Dosages for adult humans envisioned by the present invention and considered to be therapeutically effective will range from between about 1 and 100 mg/kg/day and preferably between about 5 and 50 mg/kg/day; however, lower and higher amounts may be more appropriate.

Animal Models of Inflammatory Diseases

The effectiveness of fibronectin polypeptides in the treatment of disease states in which aberrant inflammation plays a detrimental role was evaluated using four representative animal models - (i) SCW-induced arthritis and granuloma formation in Lewis rats; (ii) genetically constructed TGF-$\beta$1-deficient mice exhibiting a wasting syndrome; (iii) a rat heterotopic heart allograft transplantation model; and (iv) a rat transient focal cerebral ischemia model.

SCW-induced arthritis in Lewis rats closely mimics many features of human rheumatoid arthritis and is recognized as an animal model of arthritis in humans (see e.g., Wilder et al., *Growth Factors*, 2, 179–188 (1990); Wilder et al., *J. Cell. Biochem.*, 45, 162–166 (1991); and Case et al., *J. Clin. Investigation*, Inc., 84, 1731–1740 (1989). Human rheumatoid arthritis and the animal model have a number of molecular and cellular aspects in common, including similarities in proteolytic enzyme production and growth factor responsiveness. In both conditions, leukocyte activation and recruitment leads to inflammation and tissue swelling and/or tissue degradation.

TGF-$\beta$1-deficient mice are created by genetic engineering and do not produce detectable amounts of either TGF-$\beta$1 RNA or protein (see Kulkarni, *Proc. Natl. Acad. Sci. USA*, 90, 770–774 (1993)). Transforming growth factor betas (TGF-$\beta$s) are 25 kd peptides produced by virtually all cells of the body and exist in mammalian species as three isoforms, TGF-$\beta$1, $\beta$2, $\beta$3. Of these, TGF-$\beta$1 is the most widespread. There are other related molecules such as bone morphogenetic protein (BMP) of which there are a number of types; therefore these represent an extended TGF-$\beta$ family. TGF-$\beta$s are known to be intimately involved in many cellular processes such as cell proliferation and differentiation, embryonic development, extracellular matrix formation, bone development, wound healing, hematopoiesis, and immune and inflammatory cell response. The modulation of immune and inflammatory responses by TGF-$\beta$s includes (i) the inhibition of proliferation of all T-cell subsets, (ii) inhibitory effects of proliferation and function of B lymphocytes, (iii) down-regulation of natural killer cell activity and the T-cell response, (iv) regulation of cytokine production of immune cells, and (v) regulation of macrophage function (Kulkarni et al., *Proc. Natl. Acad. Sci. USA*, 90, 770 (1993)).

Two to three weeks after birth, TGF-$\beta$1-deficient mice experience a wasting syndrome and the mice succumb shortly after becoming symptomatic. Histopathological analysis of the tissues from the symptomatic animals reveals inflammatory lesions with massive infiltration of lymphocytes and macrophages in many organs and, particularly, in the heart and lungs. Many of the lesions resemble those found in autoimmune disorders, e.g., graft-vs.-host disease, and in certain viral diseases. The inflammatory lesions in the organs of TGF-β1-deficient mice are associated with excessive leukocyte infiltration into the organs. The lungs typically exhibit a severe phlebitis with perivascular cuffing and a mixed lymphocyte/monocyte infiltrate similar to that observed in humans with ARDS. Within the heart, mononuclear phagocyte attachment and infiltration predominates and is associated with pathology in the endocardium, myocardium and pericardium.

Mice lacking a functional TGF-β1 gene also develop inflammatory lesions in their salivary glands reminiscent of Sjögren's-like lesions. The pathology within the salivary glands of TGF-β1 (-/-) mice leads to glandular dysfunction and, as a consequence, appears to contribute to the premature demise of the mutant mice. The inflammatory lesions within the parotid and submandibular glands appear initially as focal accumulations of lymphocytes in the immediate vicinity of the ducts (see e.g., FIG. 15A, 15B illustrating the accumulation of mononuclear cells, primarily lymphocytes within the submandibular glands). As the mutant mice become symptomatic, the salivary gland lesions become more prominent and dispersed within the glandular tissue, with atrophy and disappearance of acini and disorganization of the tissue. Many of the phenotypic characteristics of TGF-β1 (-/-) mice salivary glands, including periductal accumulation of lymphocytes and plasma cells, increased numbers of Ig-positive cells, increased proliferative indices, enhanced cytokine expression, are similar to features typical of autoimmune lesions in human Sjögren's syndrome and in autoimmune mouse models (see e.g., Fox et al., *Rheum. Disease Clin. N.A.,* 18, 517–538 (1992); Fox et al., *J.Immunol.,* 152, 5532–5539 (1994); and Haneji et al., *J.Immunol.,* 153, 2769–2777 (1994); Table II presents a comparison of symptoms in the salivary glands of TGF-β1 (-/-) mice and patients with Sjögren's syndrome). Elevation in MHC antigen expression and serum autoantibodies provide further support for autoimmune mechanisms in the disease process. Epithelial hyperplasia is also evident in the salivary gland of some null mice (Boivin et al., *Am.J.Path.,* 146, 276–288 (1995)) and aggregations of cells within the inflammatory lesions of the submandibular gland are reminiscent of myoepithelial islands, features diagnostic of Sjögren's disease.

TABLE II

| Phenotype | TGF-β1 (-/-) | Sjögren's Syndrome |
|---|---|---|
| Periductal Inflammation | + | + |
| Xerostomia | + | + |
| Autoantibodies | + | + |
| Acinar Atrophy | + | + |
| Necrosis | +/- | + |
| Cytokine production | + | + |
| Increased MHC | + | + |
| Epimyoepithelial Islands | +/- | + |
| Keratoconjunctivitis sicca | + | + |

Immunoglobulin synthesis is increased in the TGF-μ1 null mice as evidenced by increased numbers of Ig-positive cells and by increased plasma Ig levels. Anti-DNA antibodies are increased in symptomatic animals and even to some degree in the young, asymptomatic mice. In addition to anti-DNA autoantibodies, polyclonal antibodies (anti-TNP and anti-ovalbumin) are also elevated.

An unusual pattern of cytokine mRNA expression, including increased IL-2, IFN-γ, and IL-10 mRNA, has been observed in salivary glands of Sjögren's patients (Fox et al., *J.Immunol.,* 152, 5532–5539 (1994)). The TGF-β1 null mice express a full array of cytokine mRNAs in the submandibular glands, similar to the Sjögren's patients. Whereas negligible amounts of IL-1 and TNF-α protein are detected in the plasma of TGF-β1 null mice, enhanced expression of IL-4 and IFN-γ protein in the plasma of TGF-β1 (-/-) mice is also observed. IL-4 and IFN-γ, products of activated T cells, influence IL-1 and TNF production by monocyte/macrophages and also induce MHC class II expression, thus enabling antigen presentation. IL-4 also promotes B cell proliferation and influences isotype differentiation by promoting class switching. Il-6 and IL-10 are also potent inducers of B lymphocyte differentiation and have been implicated in the pathophysiology of systemic lupus erythematosus (see e.g., Llorente et al., *Eur. Cytokine Netw.,* 4, 421–430 (1994); Nagafuchi et al., *J.Immunol.,* 151, 6525–6534 (1993)). Thus, B lymphocyte hyperactivity in the TGF-β1 null mice, as evidenced by increased Ig-positive cells and plasma cell, MHC expression, proliferative indices, and autoantibody production, may result from cytokine dysregulation.

A standard model of heterotopic cardiac allograft rejection has previously been developed in the rat (for a general description of the model, see Ono et al. *J. Thoracic and Cardiovascular Surgery,* 57, 225–229 (1969)). This allograft rejection model involves transplanting a donor heart into the abdomen of a recipient animal (see methods section for details of the surgical procedure) and has been used to examine the potential of new therapies to treat graft rejection.

Using this model, heart rejection occurs 6 to 7 days post transplant. The infiltration of leukocytes during the rejection process has been characterized and corresponds to the white blood cell influx seen during human organ rejection. In both human rejection and the animal allograft model, a predominately mononuclear infiltration of leukocytes (i.e. monocytes and lymphocytes) plays a prominent role prior to organ failure and death.

The experiments described below use the rat heart allograft model to assess the following endpoints: infiltration of white blood cells, tissue rejection (i.e. myocyte damage), and expression of endothelial cell-leukocyte adhesion proteins (i.e. E and P selectin, ICAM-1, and VCAM-1). Fibronectin peptides were used as intravenous pharmacological agents both as a mixture of 3 peptides or as single peptides.

While the model involves the transplantation of allograft hearts, the treatments and results have implications for other transplant organs, such as kidney, lung, pancreas, and liver. The same drug therapies and doses are commonly used to inhibit the graft rejection process in a number of different organs. The universal use of cyclosporin is a good example.

A model for transient focal cerebral ischemia has been developed in the rat (see Matsuo et al., *Stroke,* 25, 1469–1475 (1994) for a general description of the model). The ischemia model involves reversible occlusion of the middle cerebral artery ("MCA") through the intravascular insertion of a nylon thread. The insertion of the thread blocks blood flow to the middle cerebral artery and results in area of regional ischemia within the brain. Neutrophil infiltration and cerebral edema formation develop in the infarcted cortex after MCA occlusion. The neutrophil infiltration has been implicated in the pathogenesis of ischemia-reperfusion injury. The ischemia model is employed to simulate ischemic injury in humans, such as the injury observed with cerebrovascular occlusive disease (cerebral infarction), myocardial infarctions, pulmonary infarctions, intestinal infarctions, renal ischemia-reperfusion injury, peripheral vascular occlusive disease, and the like.

The invention will be further described by reference to the following detailed examples.

EXAMPLES

Methods

Reagents

Fibronectin peptides were coupled to ovalbumin (OA; chicken egg, grade III, Sigma, St. Louis, Mo.) by dissolving equal amounts of lyophilized peptides (2–10 mg) and OA in a small volume of water (0.5–2 ml). In a second tube, ten times the amount of peptide of 1-ethyl-3-(3-dimethylaminopropyl)-carbodiimide hydrochloride (EDC) was dissolved in water (300 $\mu$l). The EDC solution was added to the peptide/OA mixture and rotated at 4 degrees for 2–18 hours. The mixture was then dialyzed into 4 L of PBS (Phosphate Buffered Saline, pH 7.4, NIH Media Unit), changing dialysis several times. Fibronectin polypeptide ovalbumin conjugates prepared contained about 4 to 5 polypeptide fragments per ovalbumin molecule as determined by radiolabelling the peptide fragments prior to coupling and then evaluating the amount bound after coupling.

An additional study was performed in which the FN peptide fragments were resuspended in PBS at a concentration of 2 mg/ml.

Animals—Lewis Rats for SCW Model

Specific pathogen-free inbred Lewis (LEW) female rats were obtained from Harlan Sprague Dawley, Inc. (Indianapolis, Ind.). The animals were approximately 100 g at the initiation of the experiments and were housed in ventilator filter units (Lab Products, Maywood, N.J.). All injections were administered with metophane anesthesia. Studies were performed following NIH-approved animal protocol.

Preparation of bacterial cell wall fragments

Group A streptococci from the American Type Culture Collection (SCW; ATCC 10389) were grown in Todd Hewitt Broth (Difco, Detroit, Mich.), harvested in log phase, washed with PBS, incubated twice at 50° C. with 4% sodium dodecyl sulfate (SDS), washed extensively to remove the SDS, and then incubated sequentially with DNase, RNase, and trypsin (4 hr at 37° C. each; Sigma). The washed cell walls were then sonicated for 70 minutes and the cell wall fragments remaining in the supernatant after 0.5 hr of centrifugation at 10,000 g were utilized for injection. The total amount of rhamnose in the cell wall-containing supernatant was determined by the Dische-Shettles method, Dische and Shettles, *J. Bio. Chem.*, 175, 595–603 (1948).

Induction, monitoring and treatment of arthritis

On day 0, each rat was injected intraperitoneally (i.p.) with an aqueous suspension of cell wall fragments containing 2.5 mg of rhamnose. In addition, each rat was injected intravenously (i.v.) with 1 mg of the coupled peptides in 0.5 ml PBS daily for five days. Control animals received an equal volume of PBS or OA. The rats were checked daily during the acute response and every other day thereafter. The severity of the arthritis manifested by each rat was determined using a "joint count" (Articular Index; AI). This score is derived by the summation of a score of 0 (normal) to 4 (maximum) for each extremity based on the degree of swelling, erythema, and distortion (maximum total score of 16). Additional studies examined the therapeutic efficacy of the peptides by administration on days 11–15, after the acute response had subsided, and at the initiation of the chronic phase.

In a parallel study, the efficacy of uncoupled FN peptides by i.v. administration in 0.5 ml PBS (1 mg) on days 0–4 was investigated.

Histologic Evaluation of Lewis rats

All rats were examined by routine histologic techniques. Joints were either fixed in 10% formalin, decalcified, sectioned, and stained with hematoxylin and eosin or quick-frozen in O.C.T. compound (Miles Scientific, Naperville, Ill.) by immersion in a mixture of dry ice and acetone, and sectioned for additional staining.

Animals—TGF-$\beta$1-deficient Mice

Transforming growth factor $\mu$1 null (TGF-$\beta$1 (−/−) mice were produced by targeted destruction of the TGF-$\beta$1 gene contained in a 5.7-kb Bgl II genomic fragment and transfection into mouse embryonic stem (ES) cells (Kulkarni et al., *Proc. Natl. Acad. Sci. USA*, 90, 770–774 (1993)). Mutated ES cells were injected into 3.5 day old blastocysts and transferred into the uterus of pseudopregnant mice (C57BL/6J) to produce chimeric heterozygous TGF-$\beta$1($\pm$) mice. Chimeras were mated to produce offspring which were homozygous for the TGF-$\beta$1(−/−) gene mutation. Mice were housed in a double-barrier virus- and pathogen-free facility. Mouse genotype was verified by PCR analysis of extracted tail DNA (Kulkarni et al., *Proc. Natl. Acad. Sci. USA*, 90, 770–774 (1993)).

Spleen, Thymus and Blood Mononuclear Leukocytes Isolation from TGF-$\beta$1(+/+), ($\pm$), and (−/−) Mice TGF-$\beta$1(+/+), ($\pm$), and (−/−) mice (littermates) were sacrificed by $CO_2$ inhalation and lymphoid tissues were aseptically isolated. Thymus and spleen tissue specimens were pressed between sterile microscope slides (to prepare single cell suspensions), filtered through sterile 4×4 12 ply gauze (Johnson and Johnson Products Inc., New Brunswick, N.J.) and centrifuged 1800 g, 10 min, 4° C.). The resulting pellets were resuspended in 10 ml of ACK lysing buffer (B & B Research Laboratories, Fiskeville, R.I.) for 10 min at 4° C. to lyse RBC, washed with PBS (1800 g, 10 min, 4° C.), and resuspended in RPMI 1640 medium (containing heat inactivated 5% FBS, 2mM glutamine, 10 $\mu$g/ml gentamycin, 50 $\mu$M 2-mercaptoethanol) before being counted on a Coulter counter (Coulter Electronics Inc., Hialeah, Fla.).

Peripheral blood mononuclear leukocytes were isolated by ficoll (Histopaque; Sigma Chemical Co., St. Louis, Mo.) centrifugation (900 g, 30 min, 23° C.) of heparinized blood diluted in PBS.

Immunohistochemistry and Histological Evaluation

Selected tissues were placed in either phosphate buffered saline (PBS), 10% neutral buffered formalin (10% paraformaldehyde in PBS), or 4% paraformaldehyde. Tissues in PBS were immediately embedded in Tissue-Tek O.C.T. Compound (Miles; Elkart, Ind.) and snap-frozen by immersion in liquid nitrogen or in a dry ice-acetone bath. Snap-frozen tissues were stored at −70° C. until used. Tissue samples fixed for at least 24 hr in 10% formalin were embedded in paraffin. Snap-frozen and paraffin-embedded tissues were sectioned (5 $\mu$M) and stained with hematoxylin and eosin for histological analysis.

Endothelial Cell Culture

Mouse pulmonary artery (MPA) endothelia cells were generously provided by Dr. Una S. Ryan (Washington University, St. Louis, Mo.) and were sustained in culture as previously described (Ryan and Maxwell, 1986, Biology of Endothelial cells). Cells were harvested mechanically for passage and subculture. Cells were seeded onto chambered slides at a concentration of $\sim 2.5 \times 10^{-4}$ cells/ml. Adhesion assay slides were usually prepared 24–48 hr (~70% confluent monolayer) prior to use.

Cell Attachment Assays

Cell attachment assays were performed using a modification of a previously reported procedure (Wahl et al., *Proc. Natl. Acad. Sci.: USA*, 90, 4577 (1993)). Tissue culture chamber slides (8-well; Lab-tek, Nunc Inc., Naperville, Ill.) were coated with purified fibronectin (33 kD fragment; 8 μg/well), laminin, or pulmonary artery endothelia cells (_70% confluence). Human plasma fibronectin was purified by sequential ion-exchange and gelatin affinity chromatography, and the tryptic/catheptic 33 kD heparin-binding fragment of the fibronectin A chain was isolated (McCarthy et al., *Biochemistry*, 27, 1380–1388 (1988)). To minimize non-specific binding of cells, bovine serum albumin (BSA; 1 mg/ml) was added to each well at 37° C. for 1 hr and aspirated before cells were seeded in replicate wells at a density of $2.0 \times 10^6$ cells/0.2 ml. After incubation for 30 min at 24° C. or 37° C., the unattached cells were removed by two PBS washes, and the attached cells were fixed and stained with Diff-Quik (Baxter Scientific Products; McGraw Park, Ill.). Attached leukocytes were quantitated using the Optomax Image Analyzer (Hollis, N.H.) and the data expressed as the mean ± SE. For inhibition assays, cells were incubated at 37° C. for 15 min in the presence and absence of fibronectin polypeptides prior to being seeded in replicate wells coated with intact fibronectin 33 kD heparin-binding fragments.

Leukocyte Infiltration in Lung and Cardiac Tissues of TGF-β1Deficient Mice

Although initially appearing normal, about 8 days post partum, mice homozygous for the TGF-β1mutation (−/−) began to exhibit leukocyte adherence to venules and tissue infiltration. Not all tissues are uniformly affected, but nearly 100% of the homozygotes exhibit both lung and cardiac pathology (Kulkarni et al., *Proc. Natl. Acad. Sci. USA*, 90, 770–774 (1993)). The lungs exhibit severe phlebitis with perivascular cuffing and a mixed lymphocyte and monocyte infiltration. Within the heart, mononuclear phagocyte attachment and infiltration are predominately observed and are associated with pathology in the endocardium, myocardium and pericardium. Increased vessels in the papillary myocardium, swollen infiltrated pericardium and the continued accumulation of macrophages nearly obliterated the myocardium contributing to the death of the mice at 3–4 weeks of age.

Adhesion of Mononuclear Leukocytes to Extracellular Matrix in vitro

In order to define the basis of the massive leukocyte infiltration into the heart, lungs and other tissues of the TGF-β1-deficient mice, lymphoid cells were isolated from (+/+) and (−/−) littermates and their adherence properties compared in vitro. Mononuclear leukocytes, whether derived from peripheral blood, thymus or spleen of the (−/−) mice, were more adherent to extracellular matrices than comparable populations obtained from either (±) or littermates. The splenocytes derived from symptomatic 21 day-old TGF-β1(−/−) mice were _300% more adherent to an intact fibronectin 33 kD heparin-binding fragments than splenocytes from littermate controls. Similarly, TGF-β1(−/−)-derived mononuclear leukocytes adhered more readily to laminin substrates than mononuclear leukocytes from littermate controls.

Adhesion of Mononuclear Leukocytes to Endothelial Cells in Culture

In parallel experiments, the interaction of mononuclear leukocytes with endothelial cell monolayers was evaluated. A nearly 200% increase in the adherence of (−/−) splenocytes relative to that observed for either (+/+) or (±) was observed. These data suggest that mononuclear leukocytes from TGF-β1-deficient mice have enhanced adherence properties which likely contribute to the adhesion and migration of these cells into the tissues of the symptomatic animals.

Fibronectin Peptide Treatment of TGF-β1-deficient Mice

Figure 4:
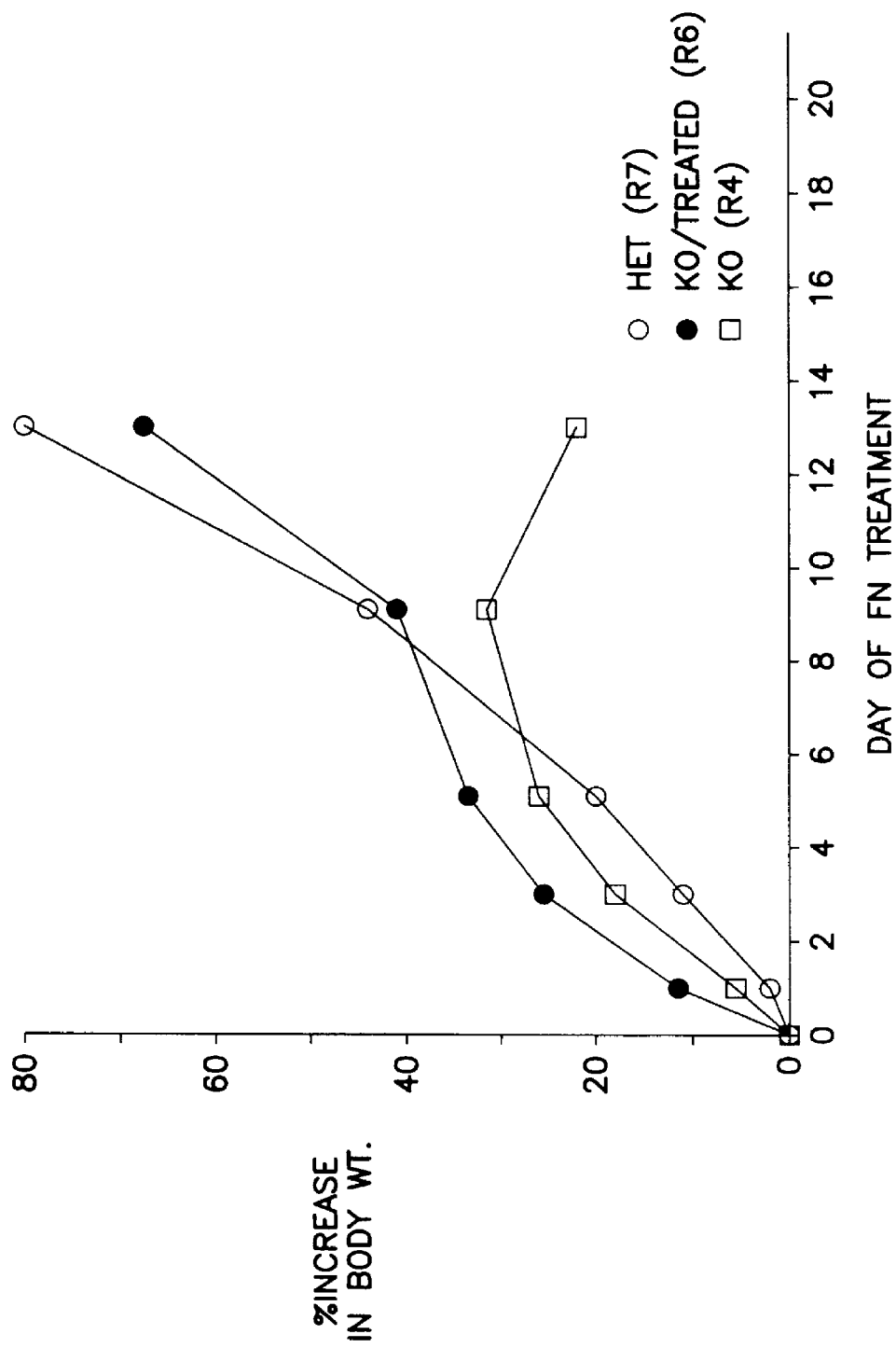
FIG. 4 shows the effect of fibronectin fragments on the weight of mice made genetically deficient in TGF-β1 (−/−) (this creates a spectrum of symptomology in affected animals). A mixture of fibronectin fragments was administered for 14–18 days intraperitoneally starting 8 days after birth. Controls included untreated TGF-β1-deficient mice (−/−) and normal wild-type TGF-β1 (+/+) mice.

Four synthetic fibronectin polypeptides (I, V, CS-1 and MC-2) were evaluated for their ability to block the adherence of TGF-β1 (−/−) leukocytes to fibronectin substrates and endothelial cell monolayers. The fibronectin polypeptides individually blocked leukocyte-fibronectin and leukocyte-endothelial cell adhesion. Based on these data, TGF-β1 (−/−) mice were injected with the active polypeptides in an effort to interrupt the widespread tissue infiltration and pathology. Since leukocyte adhesion to the vessel wall becomes evident on or around day 8 post partum, a mixture of four fibronectin synthetic polypeptides (FN-I [SEQ ID NO: 1], FN-V [SEQ ID NO: 3], CS-1 [SEQ ID NO: 4], and MC-2 [SEQ ID NO: 6]) were administered intraperitoneally daily beginning on day 8 for 14–18 days. Confirmed TGF-β1-deficient mice (by PCR analysis of tail DNA) were treated with a combination of the four fibronectin polypeptides at a total concentration of 4 mg/ml (prepared by dissolving 1 mg of each of the four polypeptides in 1 ml of solution). The mice (8 days-old) received a daily intraperitoneal injection (0.4 mg/0.1 ml) of the FN peptide cocktail. Even though asymptomatic, mice were documented to be TGF-β1-deficient mutants by PCR analysis of tail DNA. Animal weight as a marker of symptomology was monitored daily and as shown in FIG. 4, peptide treatment was able to retard the typical plateau and loss of weight evident in the untreated homozygote TGF-β1-deficient animals. Three of three animals receiving this treatment showed diminished weight loss as well as a reduction in other symptoms.

Figure 5A:
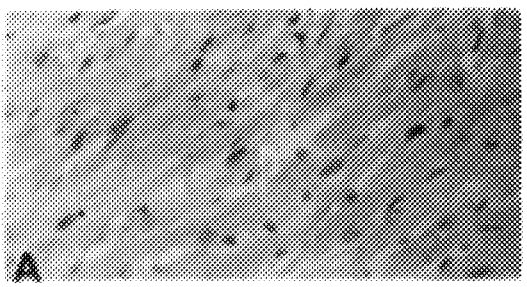
FIGS. 5A to 5C shows the effect of fibronectin fragments on the infiltration of inflammatory cells into heart tissue of TGF-β1-deficient mice.
Figure 5C:
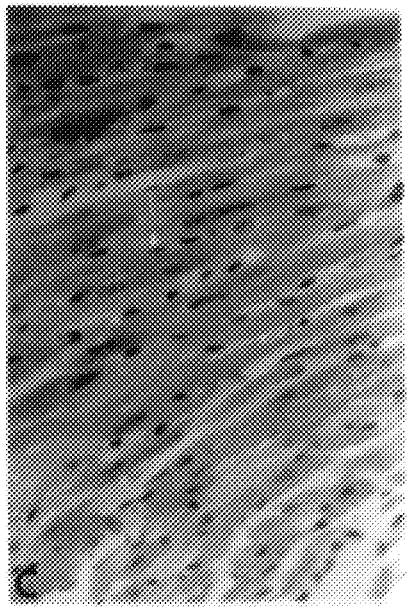
Figure 5B:
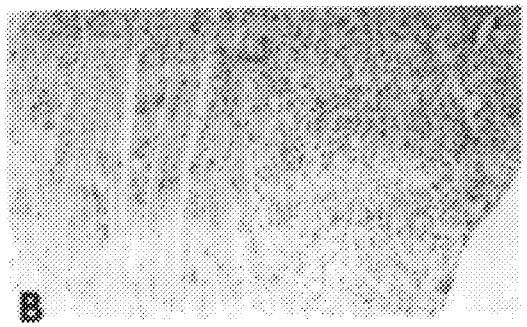
Figure 6A:
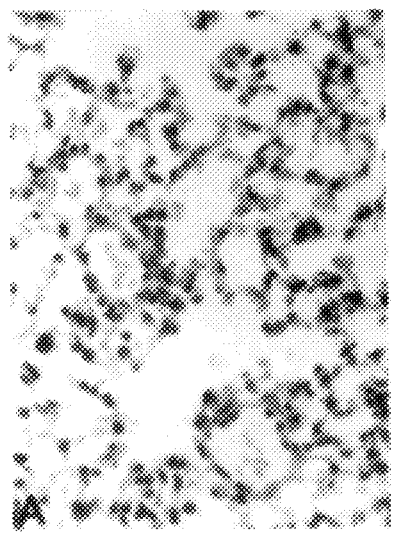
FIGS. 6A to 6C shows the effect of fibronectin fragments on the infiltration of inflammatory cells into lung tissue of TGF-β1-deficient mice.
Figure 6B:
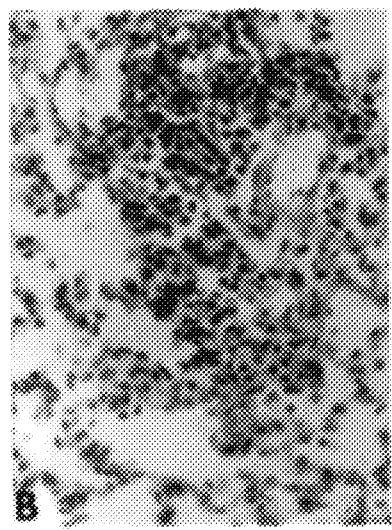
Figure 6C:
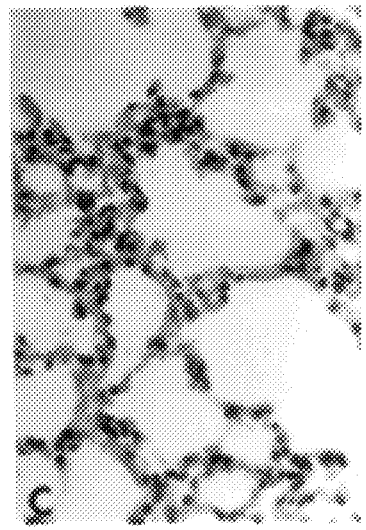

To evaluate the impact of the fibronectin polypeptides on the evolution of tissue pathology in these animals, the mice were sacrificed and tissues processed for light microscopic and ultrastructural analysis. Three experiments were run and for each experiment all of the mice (untreated (−/−), FN treated (−/−) and wild-type (+/+) control) were sacrificed when the untreated TGF-β1-deficient littermate (−/−) was close to succumbing. As represented by the heart (FIG. 5), but also evident in the lung (FIG. 6), fibronectin polypeptide administration resulted in a virtual block of leukocyte infiltration into the tissue. Whereas the homozygous littermate (−/−) which received no polypeptides exhibited characteristic massive numbers of inflammatory cells in the pericardium and myocardium (FIG. 5B), the heart from the TGF-β1-deficient littermate which was the recipient of daily intraperitoneal peptide therapy contained few, if any, inflammatory cells (FIG. 5C) and appeared more like heart tissue of the normal wild-type (+/+) control (FIG. 5A). This striking effect of the synthetic polypeptides on cardiac pathology was paralleled by reduced infiltration of leukocytes into the lung. (Compare the massive infiltration of inflammatory cells observed in the lung tissue of untreated TGF-β1-deficient mice (FIG. 6B) with the lung tissue of the normal wild-type control (FIG. 6A) and the TGF-β1-deficient littermates which received daily i.p. fibronectin peptide therapy (FIG. 6C)).

TGF-β1 Deficient Mice Salivary Gland Related Analyses Histochemistry

Parotid, sublingual, and submandibular salivary glands were removed from TGF-β1 (−/−) mice and their normal littermates, fixed in 4% paraformaldehyde for 4 hr and embedded in paraffin. Sections (5 μm) were stained with hematoxylin and eosin (H & E) for histopathology. For electron microscopy, the glands were fixed in 2% glutaraldehyde/2% formaldehyde and embedded in plastic. Mouse IgG was detected by ABC (avidin biotin peroxidase-complex) immunohistochemistry on Bouin's fixed tissue using a biotinylated anti-mouse IgG (Vectastain Mouse Elite kit, Vector Laboratories, Burlingame, Calif.) without the primary antibody.

Cell Proliferation

Tissue sections were stained with a mouse monoclonal anti-proliferating cell nuclear antigen (PCNA) (1:400, DAKO Corp., Carpinteria, Calif.) with Vectastain ABC mouse kit (Vector Laboratories) to identify cells in S phase of the cell cycle. Cyclin-dependent kinase (CDK) concentrations in protein extracts of homogenized salivary glands were determined by using a commercial Elisa Kit (Paracelsian, Ithaca, N.Y.). CDK mRNA was detected by Northern analysis using a p34cdc2 probe (American Type Culture Collection, Rockville, Md.).

Autoantibody Assay

Plasma dilutions were incubated on DNA-coupled microtiter plates for 2 h. After washing, alkaline phosphatase-conjugated anti-mouse IgM was added for 2 h. Antibody concentrations were determined from a standard curve using a high-titered antisera (Shirai et al., $Immunol.$ $Today$, 15, 527–532 (1994)).

Reverse Transcriptase-PCR (RT-PCR)

Total RNA was isolated from submandibular glands with guanidine isothiocyanate and reverse transcribed (as described in Christ et al., $J.$ $Immunol.$, 153, 1936–1946 (1994)). The cDNA was amplified by PCR using the following conditions: 94° C. for 45 s, 60° C. for 45 s, 72° for 2 min except for IL-6 (93° C. for 1 min, 60° C. for 2 min, 72° C. for 1 min) and GAPDH (94° C. for 1.5 min, 50° C. for 1.5 min, 72° C. for 2 min). Cycle number was selected based upon a linear dose-response curve: IL-1β (29 cycles), IL-2 (30 cycles), IL-2R (35 cycles), IL-4 (35 cycles), IL-6 (30 cycles), IL-10 (32 cycles), TNF-α (29 cycles), γ-IFN (42 cycles), GAPDH (28 cycles). The IL-1β, IL-2, IL-2R, TNF-α, and IFN-γ primer sets were obtained from Clontech (Palo Alto, Calif.). The IL-6 and GAPDH sequences have been described previously (Montgomery et al., $J.$ $Immunol.$, 147, 554–560 (1991)); Christ et al., $J.$ $Immunol.$, 153, 1936–1946 (1994)). The IL-19 primer sequences are as follows (5' to 3'):

sense: CTGCTCTTACTGACTGGCATGA (SEQ ID NO:7)

antisense: TCAAATGCTCCTTGATTTCTGGGC (SEQ ID NO:8)

PCR products were analyzed by Southern hybridization using radiolabelled cDNA (IL-2, TNF-α, IFN-γ, GAPDH) or specific internal probes (IL-1β: 5'-AGCTTTCAGCT CATATG-GGTCCGACAGCAC-3' (SEQ ID NO:9); IL-2R: 5'-CTTCTGCATGTCTGTTGTGGTTTGT-TGCTC-3' (SEQ ID NO:10); IL-4: 5'-GTCGCATCCGTGGATATGG CTCCTGGTACA-3' (SEQ ID NO:11); IL-6: 5'-CATTTCCACGATTTCCCA-3' (SEQ ID NO:12); IL-10: 5'-GGAGTCGGTT-AGCAGTATGTTG-3' (SEQ ID NO:13)). Blots were exposed to phosphor plates and analyzed by a phosphorimager (Molecular Dynamics, Sunnyvale, Calif.) using ImageQuant, and reproduced using MDImage and MacDraw software.

Saliva Collection

Mice were injected i.p. with isoproterenol (2 μg/g body weight) and pilocarpine (0.5 μg/g body weight). Saliva was collected for 10 min using small filter strips, changing strips every 2.5 min (total of 4 strips) and storing in capped preweighed tubes to prevent evaporation. Values represent volume of saliva (1 μl =1 mg).

Evidence for Autoimmune Etiology of Salivary Gland Lesions in TGF-β1 Null Mice

The salivary gland lesions in TGF-β1 (−/−) mice closely resembled Sjögren's lesions, suggesting autoimmune mechanisms. As is characteristic of Sjögren's syndrome, autoantibody production and deposition were observed in the TGF-β1 null mice. Abundant numbers of IgG-positive cells were present in the periductal inflammatory lesions of the TGF-β1 (−/−) submandibular gland. Immune deposits were also evident in the parenchyma of the TGF-β1 (−/−) submandibular gland, but not the normal littermate. Further evidence for autoantibody production in the null mice was provided by measurements of circulating anti-DNA antibodies. Increased levels of anti-nuclear antibodies were detected in plasma from TGF-β1 (−/−) mice as compared to normal littermates (see FIG. 16). The levels of anti-DNA antibody varied widely between symptomatic null mice, with titers ranging from 28 to 280 as compared to 14 to 45 for the littermate controls. However, within each litter, autoantibody titers of the TGF-β1 (−/−) plasma was consistently higher than the titer of the normal littermate plasma (+/+). Surprisingly, asymptomatic null mice, ranging in age from 3 days to 11 days, also showed elevated autoantibody expression as compared to normal littermate controls.

Constitutive Proliferation of Inflammatory Cells in Salivary Glands of TGF-β1 Null Mice The massive accumulation of lymphocytes and plasma cells within the salivary gland and enhanced production of antibodies suggested that the cells within the salivary gland were highly activated. To quantitate lymphoproliferation within the salivary gland of the TGF-β1 (−/−) mice, tissue sections were stained with anti-PCNA antibody to identify cells in the S phase of the cell cycle. A large number of cells in the lesions surrounding the ducts as well as scattered cells within the parenchyma stained positive for PCNA. Evidence for actively dividing cells was also provided by expression of cyclin-dependent kinase ("CDK"), an enzyme that increases in the $G_o$ to $G_1$ transition and throughout the $G_1$ phase of the cell cycle. CDK levels were elevated in the salivary glands of TGF-β1 (−/−) mice versus normal littermates (see FIG. 17). CDK (p34cdc) mRNA was also increased in the salivary gland of TGF-β1 (−/−) mice. CDK was also dramatically elevated in the lymph nodes of TGF-β1 (−/−) mice (see FIG. 17), consistent with a lymphoproliferative disorder.

Cytokine mRNA Expression in Submandibular Glands of TGF-β1 Null Mice

To further assess the activation potential of the infiltrated cells, cytokine mRNA expression in submandibular glands of symptomatic TGF-β1 null mice and their littermates was evaluated by reverse transcriptase-PCR (FIG. 18). Increased expression of TNF-α, IL-1β, and IL-6 was observed in freshly isolated submandibular gland tissue from TGF-β1 (−/−) mice as compared to wild-type (+/+) and heterozygous (±) littermates, indicative of activated inflammatory cells. TH1 cytokines IFN-γ and IL-2 and its receptor, as well as TH2 cytokines IL-4 and IL-10, were also elevated in the submandibular glands of TGF-β1 knockout mice. In several cases, elevated levels of specific cytokine mRNAs were detected in heterozygous mice even though the mice were phenotypically normal. Low amounts of some cytokines (IFN-γ and IL-4) were detected in the plasma of the TGF-β1 null mice.

Reduced Saliva Production in TGF-β1 Null Mice

The combination of inflammation and disruption of tissue architecture suggested that the function of the salivary glands could be affected in the TGF-β1 knockout mice.

Salivation was measured in asymptomatic and symptomatic mice following treatment with pilocarpine and isoproterenol to stimulate the flow of saliva. Little, if any, saliva could be measured in 8-day-old normal mice after treatment with pilocarpine and isoproterenol. By two weeks of age, salivation could be stimulated in normal mice and was evident within 4–7 min after drug treatment. Comparable amounts of saliva were collected within a 10-minute period from TGF-β1 (+/+) and (±) mice (35.2±7.5, n=5 and 36.5±14.8, n=6 respectively). In contrast, TGF-β1 (−/−) mice produced significantly less saliva than wild-type or heterozygous mice (17.5±5.4, n=5, p <0.05), suggesting that the salivary glands of the knockout mice are not fully functional.

Fibronectin Treatment—Effect on Salivary Glands

Mice received daily i.p. injections (0.4 mg/100 μl) for 14–19 days of a cocktail of equal amounts of four fibronectin polypeptides (FN-I [SEQ ID NO: 1], FN-V [SEQ ID NO: 3], CS-1 [SEQ ID NO: 4], and MC-2 [SEQ ID NO: 6]). Salivary glands were fixed in 10% formalin, paraffin embedded and stained with H&E for evaluation.

Animals—Rat Heterotolic Allograft Heart Transplant Model

Brown Norway donor hearts were transplanted into Lewis recipient animals. Donor hearts were flushed in situ with cold saline and stored in iced saline until the time of transplantation. Ischemia time was held constant at 1 hour (cold Ischemia) for all experiments. The reperfusion period for all treated and untreated animals was 3 days (72 hours). Injection of fibronectin peptides (either as a mixture or as individual peptides) was performed intravenously 20 minutes prior to transplantation and once every 24 hours, in animals receiving three doses of peptide.

Tissues were removed, snap frozen in liquid nitrogen, and stored at −80 C. until analyzed using standard molecular techniques for RNA extraction and Northern Blot analysis. The results for each group are presented in the Results section.

Histologic Evaluation of Transplanted Hearts

All rat hearts had a section of tissue removed just prior to snap freezing. Heart tissue sections were fixed in 10% formalin for analysis by routine histologic techniques using hematoxylin and cosin stains for light micrography.

Tissue sections were examined by a cardiac pathologist who was uninformed with respect to treatment. Tissues were scored by two criteria. A scale of 1 to 4 was used to asses the inflammatory infiltrate (i.e. influx of white blood cells). In addition organ rejection was assessed by myocyte damage. An inflammatory grade of 3 or 4 was always associated with rejection. An inflammatory grade of 0–2 could be seen without concomitant organ rejection.

Animals—Rat Transient Focal Cerebral Ischemia Model

Sprague-Dawley (SD) rats weighing 270–350 g, were divided into four groups for the following treatments: (1) induction of ischemia only, (2) administration of mixture of three fibronectin polypeptides (FN-V [SEQ ID NO: 3], CS-1 [SEQ ID NO: 4], and MC-2 [SEQ ID NO: 6]) at a total dose of 4.5 mg, (3) administration of vehicle only. The polypeptide mixture (containing 1.5 mg of each FN polypeptide) was administered intravenously as a solution in 0.45 cc saline ("vehicle"). The dose of the polypeptide mixture (or vehicle alone) was administered 30 minutes prior to induction of ischemia, just after reperfusion, 3 hours after reperfusion, and 24 hours after reperfusion. Neurological status during recovery was assessed and the animals were sacrificed 48 hours after surgery. The brains were then removed and processed for histology to determine infarction size according to the procedure described below.

The animal procedures were carried out under complete, general anesthesia. Anesthesia was induced with intraperitoneal injection of a mixture of ketamine, 100 mg/ml; xylazine, 20 mg/ml; and acepromazine, 10 mg/ml at a dose of 1.5 ml/kg and maintained throughout the operation with a 1 to 2% halothane and 70% $N_2O$ mixture. The rectal temperature was maintained constant between 37° and 38° C. with heating pads. The left femoral vein was cannulated for administration of peptides.

An incision was made in the midline of the neck and the left carotid bifurcation exposed. The common carotid artery was then occluded, and the branches of the external carotid artery were dissected and divided. The internal carotid artery was followed rostrally, and the pterygopalatine branch was identified and divided. An occluder was then advanced from the external carotid artery into the lumen of the internal carotid artery until the origin of the middle cerebral artery was blocked. A 4-0 nylon suture with its tip coated with silicone to a diameter of 0.25mm was used as the occluder. Reperfusion was accomplished by withdrawal of the suture until the tip was observed in the internal carotid artery lumen.

A neurological examination (as described in Zea Longa et al., *Stroke*, 20, 84–91 (1989)), was performed 12, 24 and 48 hours after occlusion. The following standard scoring scale was used in the neurological examination: 0, normal, 1, failure to extend the left forepaw; 2, circling to the left; 3, falling to the left; and 4, does not spontaneously exhibit a consciousness disturbance.

Measurement of infarct size

Ischemic animals were anesthetized with the mixture described above (mixture of ketamine, xylazine and acepromazine) after 48 hours of reperfusion. The brains were removed from the animals and kept at −70° C. for five minutes. Each frozen brain was cut into 2–mm-thick coronal blocks, for a total of seven blocks per brain. The brain slices were incubated at 37° C. for 30 minutes in 2% 2, 3, 5-triphenyl-2H-tetrazolium chloride (TTC) and placed in 10% formalin for 48 hours. The unstained regions have been shown to correspond well to regions of histopathological infarction. The surface of each slice was digitized, and total surface area and the infarcted surface area were calculated using Jandel PC3D three-dimensional reconstruction software (Jandel, Corte Madera, Calif.). The total and infarcted volume was calculated for each slice by multiplying the surface area by the slice thickness.

RESULTS

Effect of FN fragments on the development of SCW-induced arthritis

Figure 1:
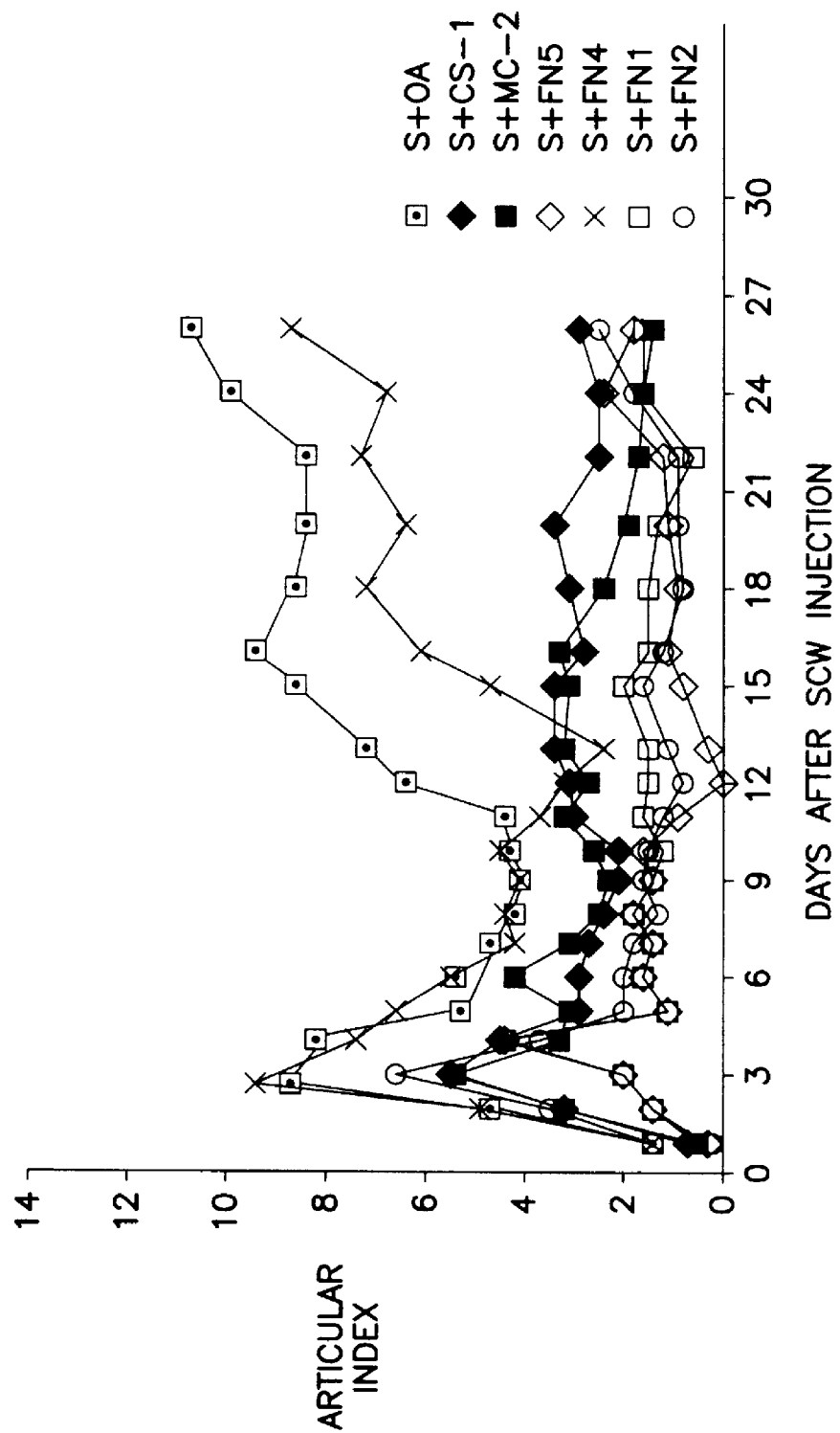
FIG. 1 shows the effect of FN fragments on SCW-induced arthritis. OA-coupled FN fragments were administered i.v. on days 0–4 to SCW-injected rats. Controls included rats given SCW and OA only. Articular indices were determined at indicated intervals (N=3–4/group).

Daily i.v. administration of OA-coupled FN peptides on days 0–4 had an inhibitory effect on the evolution of arthritic lesions. The acute, neutrophil-mediated phase was blunted, but more dramatic was the suppression of the chronic, destructive phase (FIG. 1). On day 3, at the height of the acute response, the articular index (AI) was 8.5±1.2 for the OA-treated, SCW-injected rats, which was reduced with treatment to 5.6±0.8 with CS-1, 5.5±0.84 with MC-2, 5.7±1.1 with FNV, 6.6±1.9 with FNII, and 2.0 ±0.9 with FNI. Under these conditions, treatment with FNIV did not suppress the acute response, with an AI of 9.2 ±0.97.

By day 27, when chronic inflammation is well established, the differences were even more pronounced. The AI of the OA-treated, SCW-injected rats was 10.5±0.3. FNIV was the least effective in suppressing arthritis (AI= 8.6±0.3). However, the other coupled peptides suppressed the AI to 2.5±0.7 for CS-1, 1.25±0.25 for MC-2, 1.7±0.5 for FNV, 2.3±0.9 for FNII and 1.5±1.1 for FNI. No evidence of toxicity based on weight loss or hematocrit levels was observed in the peptide-treated groups.

Effect of FN fragments on the evolution of chronic arthritic lesions

Figure 2:
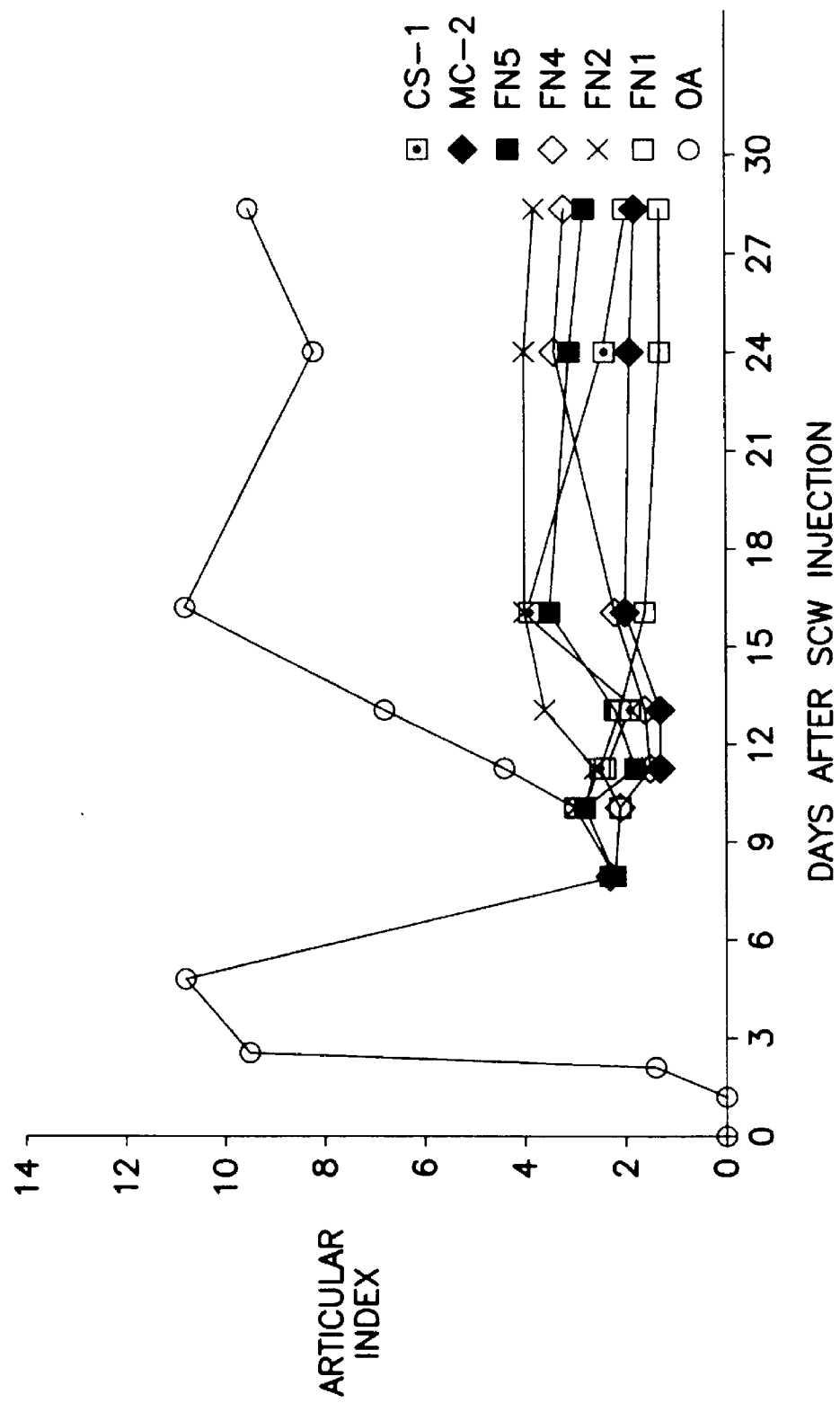
FIG. 2 shows the effect of FN fragments on chronic synovitis. OA-coupled FN fragments were administered i.v. on days 11–15 to SCW-injected rats. Control SCW-injected rats received OA. Articular indices were determined at indicated intervals (N=3–4/group).

To determine if the peptides could therapeutically suppress the chronic synovitis, administration was initiated after the acute response had fully developed. All the animals were randomized so that the AI for each group was similar, and peptide administration was started on day 11 and continued daily until day 15 (5 days), well into the chronic phase. Surprisingly, all the FN peptides were suppressive (FIG. 2). On day 28, the OA-treated SCW-injected group had an AI of 11.3±0.5. Treatment with CS-1 reduced the AI to 4.2±1.5, MC-2 reduced it to 2.7±1.9, FNV to 4.5±1.0, FNIV to 2.0±1.0, FNII to 4.9±1.2, and FNI to 1.5±1.0. Based on these data, the primary target at this stage appears to be of leukocyte lineage (lymphocytes and/or macrophages) which are the central mediators of the chronic cell-mediated phase of arthritis in this model (Allen et al., *J. Clin. Invest.*, 76: 1042–1056 (1985); and Wahl et al., *J. Exp. Med.*, 168: 1403–1417 (1988)).

Effect of uncoupled FN fragments on the development of SCW-induced arthritis

Figure 3:
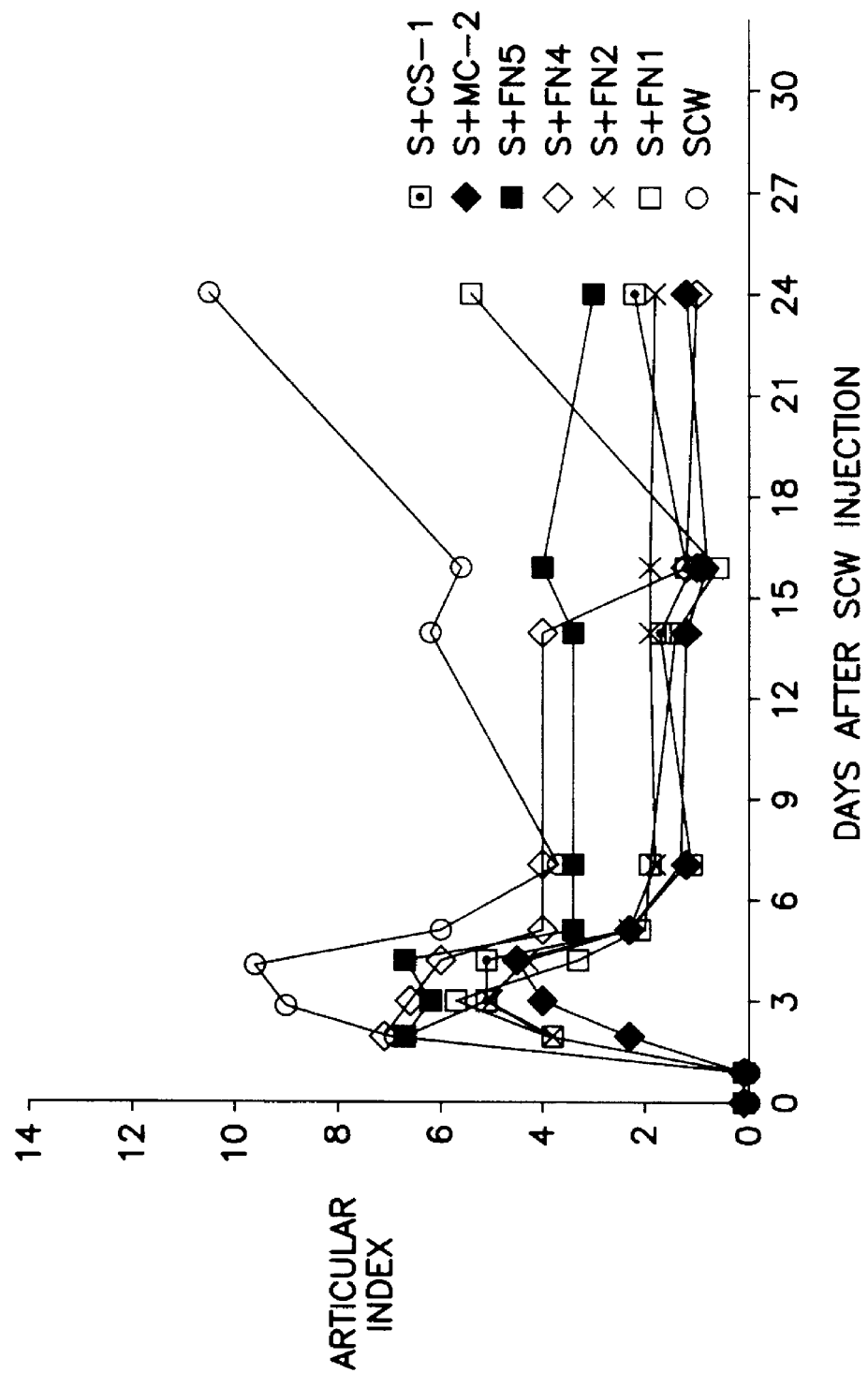
FIG. 3 shows the effect of uncoupled FN fragments on SCW-induced arthritis. FN fragments were administered i.v. on days 0–4 to SCW-injected rats. Controls included rats injected with SCW only. Articular indices were determined at indicated intervals (n=1–3/group).

Daily i.v. administration of uncoupled FN peptides on days 0–4 suggested an inhibitory effect on the development and maintenance of arthritis. In initial studies, the acute phase was slightly suppressed by all fragments (FIG. 3). On day 4, at the peak of the acute response, the AI of the untreated rats was 9.5, compared to a range of 3.3 to 6.7 after treatment with the FN fragments. Furthermore, the effect was sustained until day 24 when the AI of the untreated arthritic rats was 9.7, compared to 2.2 for the CS-1 treated animals, 1.3 after MC-2 treatment, 2.8 after FNV treatment, 1.0 after FNIV treatment, 1.7 after FNII treatment, and 5.0 after FNI treatment. These data show that the uncoupled FN fragments, in addition to multivalent FN peptides coupled to carriers or polymers (e.g., OA), are effective in suppressing SCW-induced arthritis.

Effect of FN fragments on the Histopathogenesis of SCW-induced Arthritis

SCW induces synovial cell lining hyperplasia with villus formation, mononuclear cell infiltration, synovial proliferation, bone erosion, and ultimately, joint destruction which follows a pattern similar to human arthritis. Following peptide administration from days 0 to 4, the joints exhibited markedly reduced histopathology when evaluated at the termination of the experiment. There was less infiltration of inflammatory cells, less synovial hyperplasia, and little evidence of erosions. In contrast, the OA-treated, SCW-injected rats exhibited the destructive joint abnormalities characteristic of untreated groups of animals. Administration of the peptides during the early chronic phase of disease also effectively reduced the chronic, destructive pathology.

Effect of FN Fragments on the Wasting Syndrome of TGF-β1-deficient Mice

The adhesion of leukocytes to the vascular endothelium is the earliest detectable event leading to tissue pathology in the TGF-β1-deficient mouse. Consistent with this adherence to the vessel wall in the target tissues, leukocytes isolated from the (−/−) homozygotes exhibit increased adherence to both extracellular matrix and to endothelial cell monolayers in vitro. Synthetic FN polypeptides (I, V, CS-1 and MC-2) individually blocked the adhesion of TGF-β1 (−/−) leukocytes to fibronectin substrates and endothelial cell monolayers in vitro.

Daily intraperitoneal administration of a mixture of four fibronectin polypeptides (I, V, CS-1 and MC-2) had an inhibitory effect on the infiltration of inflammatory cells into the heart and lung tissues of TGF-β1-deficient mice. The fibronectin polypeptide treatment dramatically suppressed the weight loss exhibited by untreated control TGF-β1-deficient mice at about day 17 (9 days after initiation of treatment; FIG. 4). The weight gain and histopathology of the TGF-β1-deficient mice treated with fibronectin polypeptides were very similar to that observed for the normal wild-type control (TGF-β1 (+/+). In some instances, histologic specimens of tissue from fibronectin polypeptide treated TGF-β1 (−/−) mice could not be differentiated from wild-type mice, necessitating a repetition of the PCR analysis to characterize the genotype of the mice.

Effect of FN Fragments on the Salivary Glands of TGF-β1-deficient Mice

The treatment of the TGF-β1 null mice with the combination of synthetic fibronectin peptides (daily systemic administration) capable of interacting with β1 integrins and/or cell surface proteoglycans effectively blocked the development of inflammatory lesions in the salivary glands of the TGF-β1 null mice (FIG. 19). Moreover, the structural architecture in the treated TGF-β1 null mice appeared normal and acinar and ductal elements were identical to those from a normal littermate. In contrast, the salivary glands from an untreated TGF-β1 null mouse displayed the characteristic periductal leukocyte accumulation with disrupted architecture and acinar atrophy associated with Sjögren's syndrome. The salivary glands in the fibronectin-treated mice are indistinguishable from those of the normal littermate. Inflammation is absent or dramatically reduced and the glandular architecture and the acini and ducts appear normal, suggesting that the structural abnormalities in the salivary gland occur secondary to the inflammation. The absence of pathology in the salivary gland of the fibronectin-treated TGF-β1 null mice further suggested that the gland was fully functional.

Effect of FN Fragments on the Rejection of Allograft Heart Transplants

The rat heart allograft transplant model was used to examine the potential of synthetic peptides corresponding to various domains of fibronectin to block white cell infiltration and expression of adhesion protein mRNA (i.e. E and P-selectin, ICAM-1, and VCAM-1). The day 3 time interval was chosen because the rejection response (i.e. infiltration of monocytes and lymphocytes as well as myocyte damage) in control allograft transplant tissues was severe at thin time interval.

A total of 5 treatment groups were used. Two groups of animals were treated using a mixture of fibronectin polypeptides. Peptide V [SEQ ID NO:3], CS-1 [SEQ ID NO:4], and MC-2 [SEQ ID NO:6] were used in groups A and B in a mixture of 1 mg of each respective peptide per injection (total volume=0.5 cc). In group A, 3 rats were treated only with a single dose of the polypeptides. The recipient animal was injected intravenously with the peptide mixture 20 minutes prior to transplantation. The donor heart was harvested at day 3 for histologic and molecular analysis. In group B, 3 rats were treated with 3 doses of the fibronectin polypeptide mixture. Intravenous ("IV") injections were performed 20 minutes prior to transplantation and once every 24 hours for the next two days (i.e. a total of 3 doses over 3 days). Three groups of animals were treated with a total of 3 IV injections of 1 mg of the individual fibronectin peptides. Groups of 3 rats were treated with fibronectin peptide V [SEQ ID NO:3] (Group C), CS-1 [SEQ ID NO:43] (Group D), and MC-2 [SEQ ID NO:6] (Group E) respectively, using the same 3 dose schedule outlined for group B.

Figure 7:
FIG. 7 shows an light micrograph of normal cardiac tissue (160 × magnification).
Figure 8:
FIG. 8 shows an light micrograph (400 × magnification) of cardiac allograft tissue from rats not subjected to the fibronectin peptide treatment. The allograft was harvested 72 hours after transplantation. The micrograph shows a dense infiltration of inflammatory cells.
Figure 9:
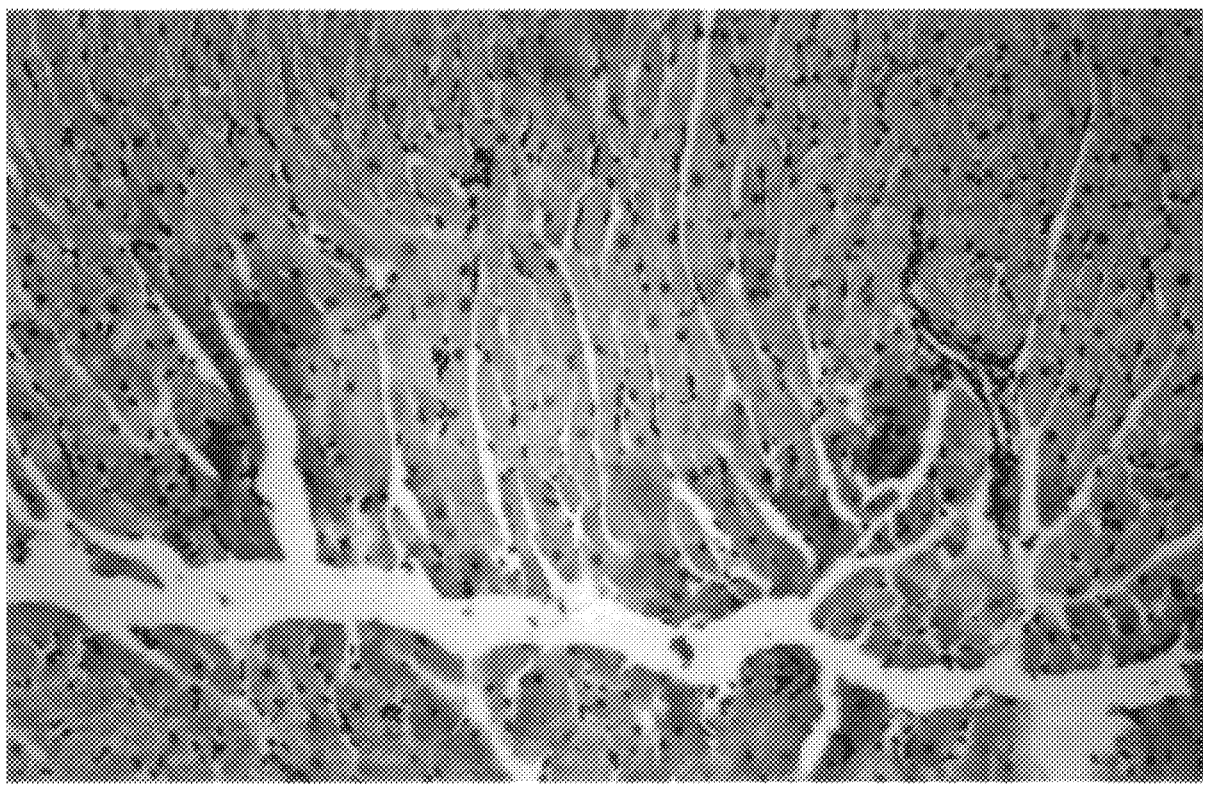
FIG. 9 shows an light micrograph (400 × magnification) of cardiac allograft tissue from rats treated once (20 minutes prior to transplantation) with the fibronectin peptides. The allograft was harvested 72 hours after transplantation. The micrograph shows no detectable inflammatory infiltration of the donor heart.
Figure 10:
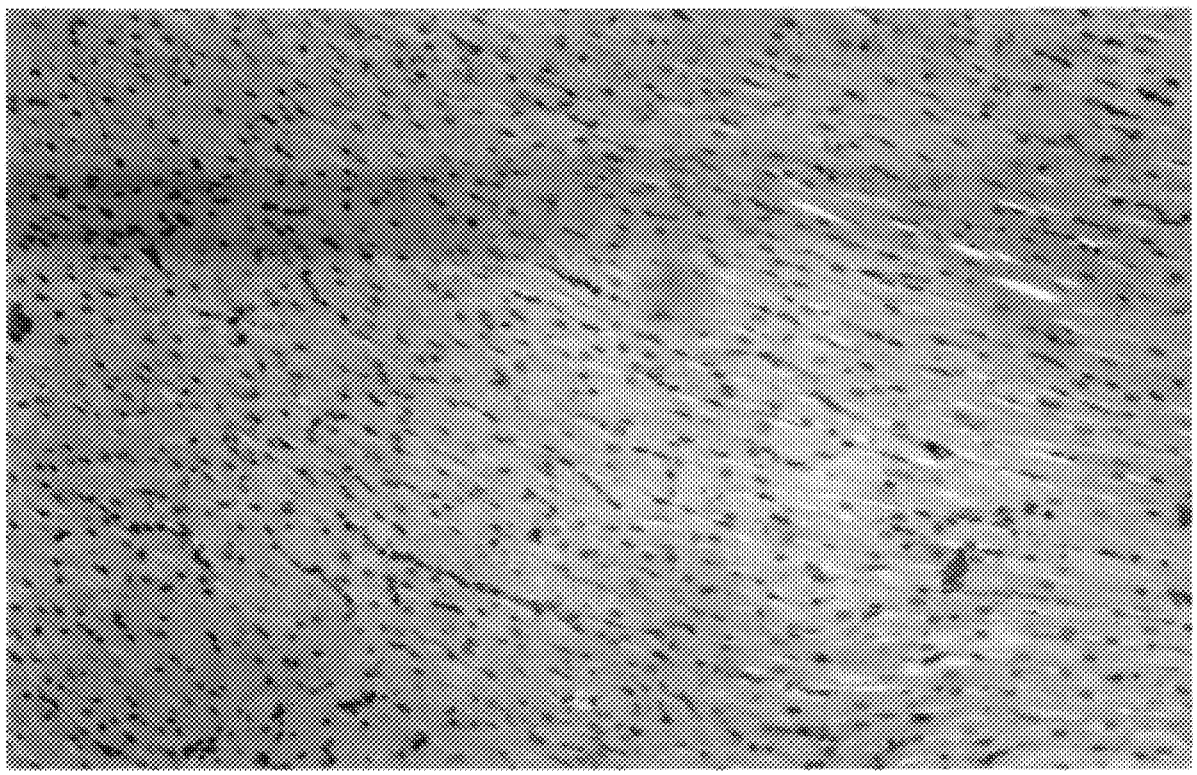
FIG. 10 shows an light micrograph (400 × magnification) of cardiac allograft tissue from rats treated three times with the fibronectin peptides. The allograft was harvested 72 hours after transplantation. The micrograph shows no detectable inflammatory infiltration of the donor heart.

Results from all fibronectin treatment groups revealed inhibition of leukocytic infiltration. In group A (single dose of the polypeptide mixture), the inflammatory response was ⅔ with minimal rejection (i.e. myocyte damage) (Compare FIG. 9 to FIGS. 7 and 8). Group B (polypeptide mixture, 3 doses) revealed 0–¼ inflammatory response and no rejection (Compare FIG. 10 to FIGS. 7 and 8). Group C (polypeptide V [SEQ ID NO:3], 3 doses) showed 1–⅔ inflammation and no evidence of rejection. Group D (polypeptide CS-1 [SEQ ID NO:4], 3 doses) and Group E (polypeptide MC-1 [SEQ ID NO:6], 3 doses) both show 1–⅔ inflammation and no rejection.

Figure 11:
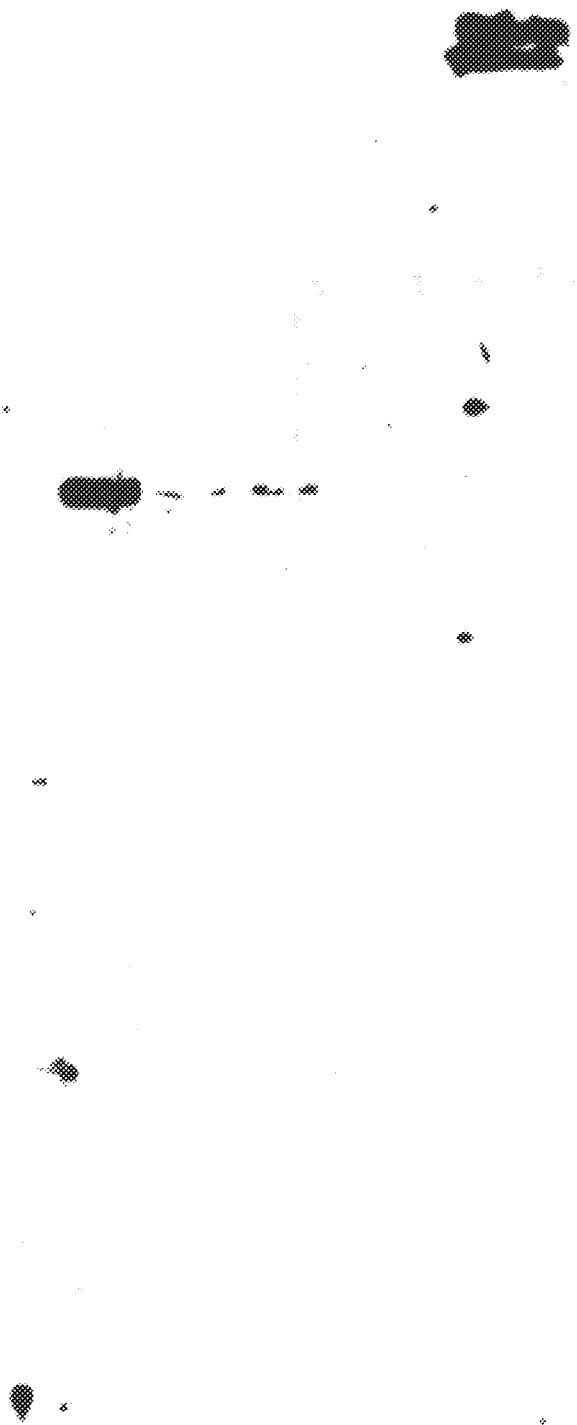
FIG. 11 shows Northern Blot analyses of P-selectin expression in cardiac tissues. The lanes correspond to (1) untreated allograft (72 hours post transplant); (2) allograft treated with a single dose of the fibronectin peptides 20 minutes prior to transplantation (72 hours post transplant); (3) allograft treated with three doses of the fibronectin peptides (72 hours post transplant); and (4) normal cardiac tissue.
Figure 12:
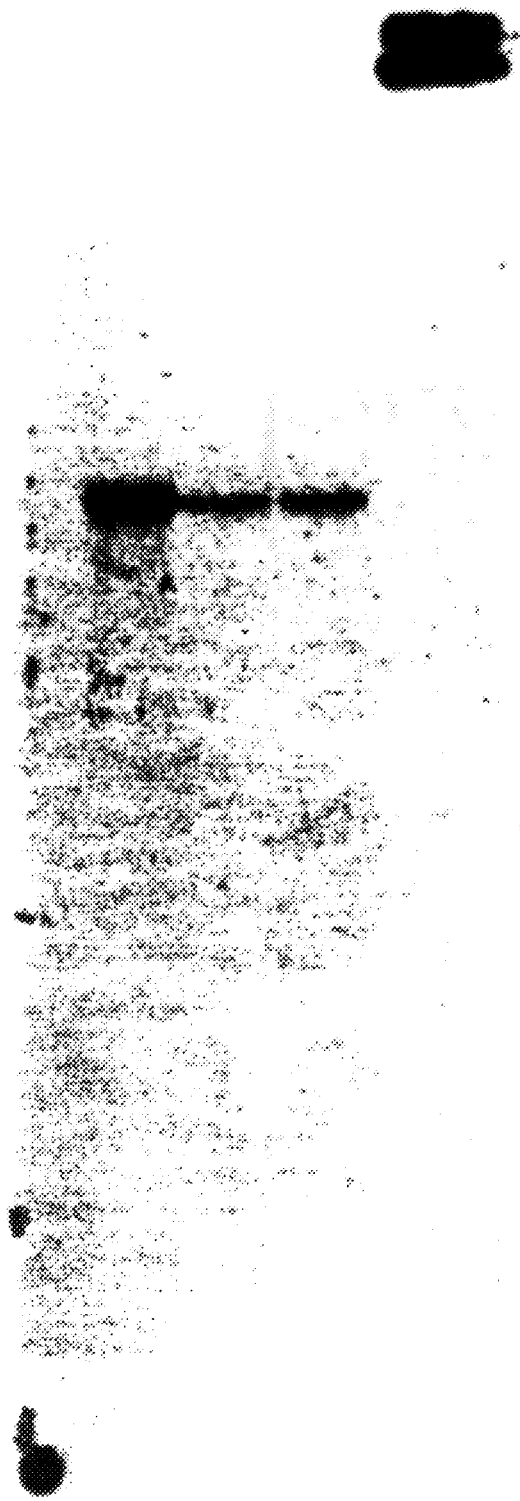
FIG. 12 shows Northern Blot analyses of E-selectin expression in cardiac tissues. The lanes correspond to (1) untreated allograft (72 hours post transplant); (2) allograft treated with a single dose of the fibronectin peptides 20 minutes prior to transplantation (72 hours post transplant); (3) allograft treated with three doses of the fibronectin peptides (72 hours post transplant); and (4) normal cardiac tissue.

Molecular analysis of mRNA expression of E-selectin, P-selectin, ICAM-1 and VCAM-1 was obtained for control untreated and fibronectin polypeptide mixture groups A & B. In the fibronectin treatment groups using the 3 dose schedule, expression mRNA for all four adhesion proteins (E-selectin, P-selectin, ICAM-1 and VCAM-1) was inhibited by about 80% compared to control untreated hearts (see FIGS. 11 and 12 for illustrations of the Northern Blot analyses of P-selectin and E-selectin expression in cardiac tissues).

Taken together, these data strongly suggest that inhibition of normal expression patterns for endothelial cell-leukocyte adhesion proteins may represent a molecular basis for the organ protection seen in the transplant model. In addition, the fibronectin V polypeptide [SEQ ID NO:3] seems to function as well as the mixture in blunting the rejection process.

Figure 13:
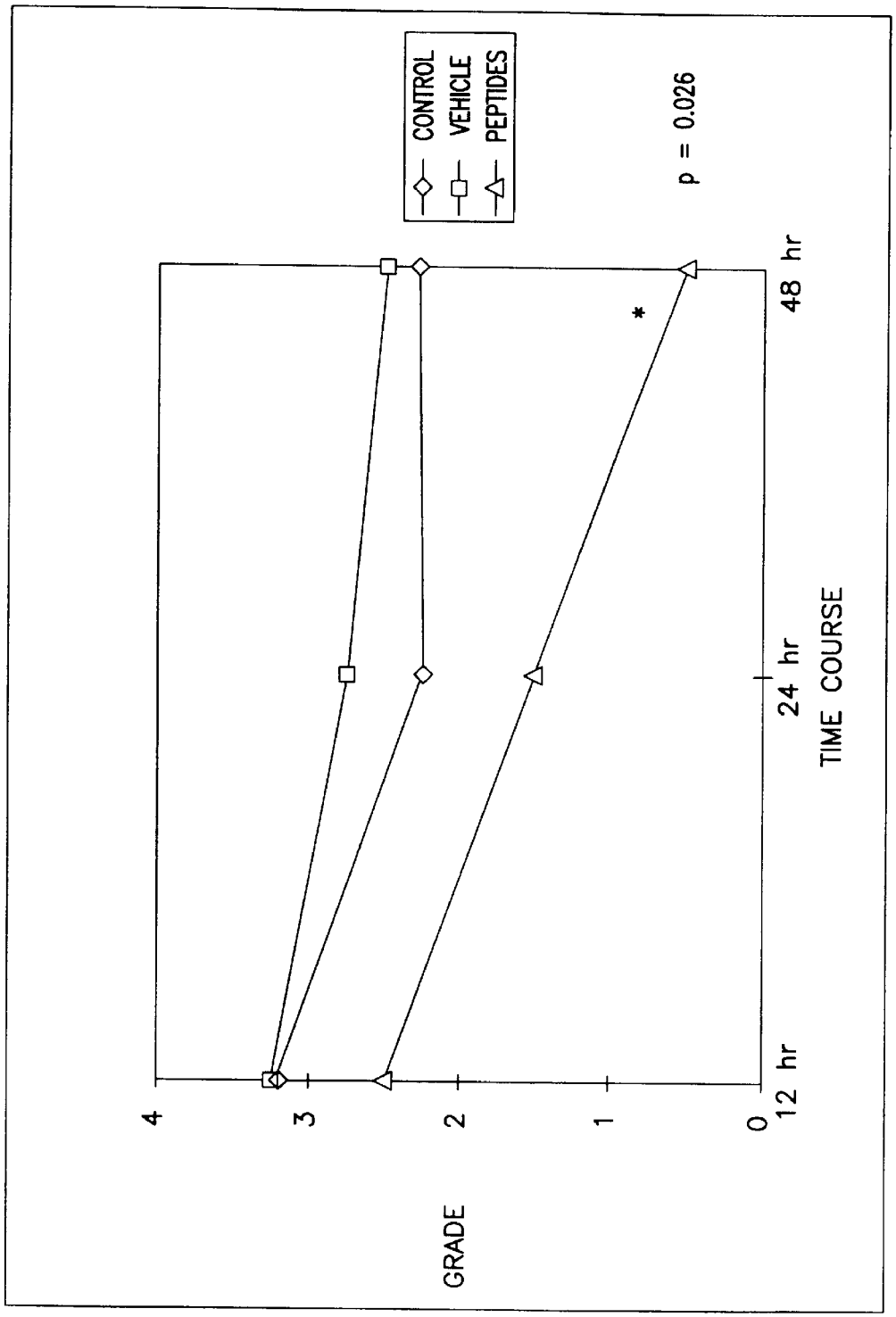
FIG. 13 shows the effect of fibronectin fragments on the neurologic deficits associated with reversible cerebral ischemia induced in Sprague-Dawley rats. The neurological status at 12, 24 and 48 hours after initiation of reperfusion is shown for (1) untreated control rats, (2) rats administered with vehicle (saline solution) only, and (3) rats administered with four doses of a mixture of three fibronectin polypeptides (FN-V [SEQ ID NO: 3], CS-1 [SEQ ID NO: 4], and MC-2 [SEQ ID NO: 6]; 1.5 mg/polypeptide per dose ). The untreated control rats were subjected to induction of ischemia and subsequent reperfusion only.

Effect of FN Fragments on Ischemic Injury in Rats Subjected to Middle Cerebral Artery Occlusion The administration of FN polypeptides 30 minutes prior to induction of ischemia, just after reperfusion, and at 3 and 24 hours after reperfusion significantly attenuated the extent of injury associated with the cerebral infarction (see FIG. 13). Neurological evaluation following the initiation of reperfusion showed a substantial decrease in the neurological deficit associated with the ischemic injury. Rats treated with a mixture of fibronectin polypeptides (FN-V [SEQ ID NO: 3], CS-1 [SEQ ID NO: 4], and MC-2 [SEQ ID NO: 6]) showed few neurological symptoms (average score circa 0.5; normal response - failure to extend the left forepaw) in contrast to moderate to severe neurological deficits (average score circa 2.5) observed in the control animals (untreated controls or rats administered with saline solution only).

Figure 14:
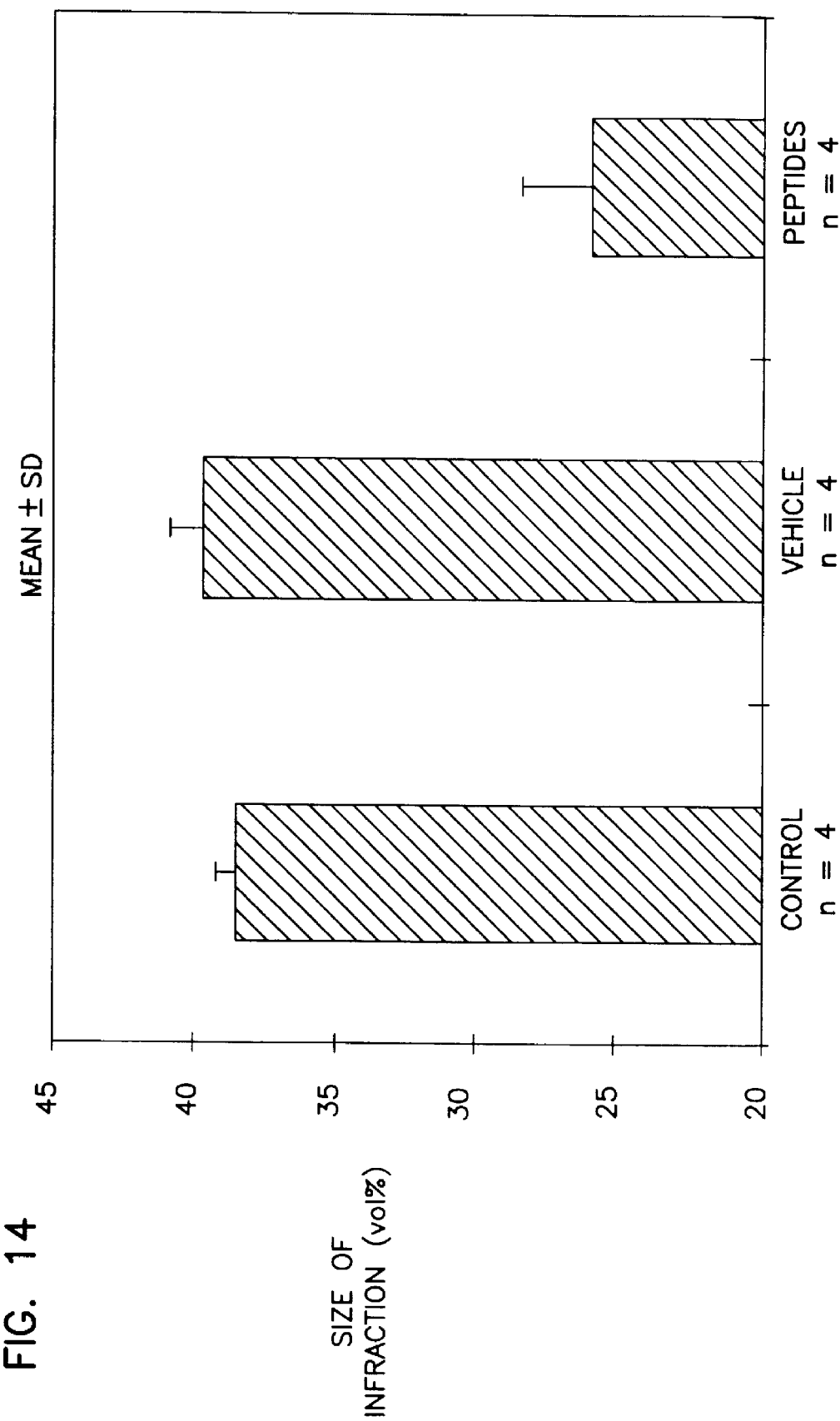
FIG. 14 shows the effect of fibronectin fragments on the infarct size induced by occlusion of the middle cerebral artery in Sprague-Dawley rats subjected to (1) induction of ischemia only (2) administration of mixture of three fibronectin polypeptides (FN-V [SEQ ID NO: 3], CS-1 [SEQ ID NO: 4], and MC-2 [SEQ ID NO: 6]) at a total dose of 4.5 mg, (3) administration of vehicle (saline) only.

Ischemic animals were sacrificed after 48 hours of reperfusion and the size of the infarct was measured. Rats treated with the mixture of three fibronectin polypeptides showed a significant (circa 35%) reduction in the size of the infarct induced by occlusion of the middle cerebral artery (see FIG. 14). The results of the experiments in the transient focal ischemia model demonstrate that fibronectin related polypeptides are capable of attenuating injury associated with ischemia, e.g., that observed with stroke, cardiac infarctions or other similar conditions.

Based on the above example and written description, it has been shown that selected peptides derived from the extracellular matrix protein, fibronectin, are effective inhibitors of acute and/or chronic inflammatory pathology. Administration of fibronectin related polypeptides with specific binding properties for integrins and cell surface proteoglycans (PG) or other CAMs can suppress acute or chronic inflammatory disorders or immune mediated disorders including autoimmune disorders. The present treatment involving the administration of fibronectin related polypeptides is particularly effective for treating rheumatoid arthritis, ARDS, ischemia, graft rejection, lupus erythematosus, Sjögren's syndrome and graft-vs.-host disease.

The invention has been described with reference to various specific and preferred embodiments and techniques. It should be understood that many variations and modifications may be made while remaining within the spirit and scope of the invention.

---

What is claimed is:

1. A method for treating ischemia in a mammal comprising: administering to said mammal an effective amount of a composition which comprises a polypeptide comprising an amino acid sequence selected from the group of tyr-glu-lys-pro-gly-ser-pro-pro-arg-glu-val-val-pro-arg-pro-arg-pro-gly-val (SEQ ID NO: 1), lys-asn-asn-gln-lys-ser-glu-pro-leu-ile-gly-arg-lys-lys-thr (SEQ ID NO: 2), trp-gln-pro-pro-arg-ala-arg-ile (SEQ ID NO: 3), asp-glu-leu-pro-gln-leu-val-thr-leu-pro-his-pro-asn-leu-his-gly-pro-glu-ile-leu-asp-val-pro-ser-thr (SEQ ID NO: 4), ser-pro-pro-arg-arg-ala-arg-val-thr (SEQ ID NO: 5), and ile-thr-val-tyr-ala-val-thr-gly-arg-gly-asp-ser-pro-ala-ser-ser-lys-pro-ile-ser (SEQ ID NO: 6), wherein the polypeptide has no more than about 100 amino acid residues.

2. The method of claim 1 wherein said mammal is a human.

3. The method of claim 1 wherein said polypeptide is administered as a conjugate which comprises at least one of said polypeptide bound to a carrier molecule.

4. The method of claim 1 wherein said polypeptide suppresses inflammation.

5. The method of claim 1 wherein said polypeptide inhibits infiltration of leukocytes into a tissue.

6. The method of claim 1 wherein said polypeptide has the formula trp-gln-pro-pro-arg-ala-arg-ile (SEQ ID NO:3).

7. The method of claim 1 wherein said polypeptide has the formula asp-glu-leu-pro-gln-leu-val-thr-leu-pro-his-pro-asn-leu-his-gly-pro-glu-ile-leu-asp-val-pro-ser-thr (SEQ ID NO:4).

8. The method of claim 1 wherein said polypeptide has the formula ile-thr-val-tyr-ala-val-thr-gly-arg-gly-asp-ser-pro-ala-ser-ser-lys-pro-ile-ser (SEQ ID NO:6).

9. The method of claim 1 wherein the polypeptide has no more than about 50 amino acid residues.

10. The method of claim 1 wherein the polypeptide has no more than about 25 amino acid residues and comprises an amino acid sequence having the formula trp-gln-pro-pro-arg-ala-arg-ile (SEQ ID NO:3), asp-glu-leu-pro-gln-leu-val-thr-leu-pro-his-pro-asn-leu-his-gly-pro-glu-ile-leu-asp-val-pro-ser-thr (SEQ ID NO:4), or ile-thr-val-tyr-ala-val-thr-gly-arg-gly-asp-ser-pro-ala-ser-ser-lys-pro-ile-ser (SEQ ID NO:6).

11. A method of treating ischemia in a mammal comprising administering to said mammal an effective amount of a composition which comprises a polypeptide having no more than about 50 amino acid residues and comprising an amino acid sequence having the formula trp-gln-pro-pro-arg-ala-arg-ile (SEQ ID NO:3).

12. The method of claim 11 wherein the polypeptide is administered as a conjugate which includes at least one of said polypeptide bound to a carrier molecule.

13. A method of treating ischemia in a mammal comprising administering to said mammal an effective amount of a composition which comprises a polypeptide having no more than about 50 amino acid residues and comprising an amino acid sequence having the formula asp-glu-leu-pro-gln-leu-val-thr-leu-pro-his-pro-asn-leu-his-gly-pro-glu-ile-leu-asp-val-pro-ser-thr (SEQ ID NO:4).

14. The method of claim 13 wherein the polypeptide is administered as a conjugate which includes at least one of said polypeptide bound to a carrier molecule.

15. A method of treating ischemia in a mammal comprising administering to said mammal an effective amount of a composition which comprises a polypeptide having no more than about 50 amino acid residues and comprising an amino acid sequence having the formula ile-thr-val-tyr-ala-val-thr-gly-arg-gly-asp-ser-pro-ala-ser-ser-lys-pro-ile-ser (SEQ ID NO:6).

16. The method of claim 15 wherein the polypeptide is administered as a conjugate which includes at least one of said polypeptide bound to a carrier molecule.

* * * * *